(12) United States Patent
Talukdar et al.

(10) Patent No.: US 11,168,084 B2
(45) Date of Patent: Nov. 9, 2021

(54) PURINE BASED COMPOUNDS AS TOLL-LIKE RECEPTOR 9 ANTAGONIST

(71) Applicant: COUNCIL OF SCIENTIFIC & INDUSTRIAL RESEARCH, New Delhi (IN)

(72) Inventors: Arindam Talukdar, Kolkata (IN); Dipyaman Ganguly, Kolkata (IN); Ayan Mukherjee, Kolkata (IN); Barnali Paul, Kolkata (IN); Oindrila Rahaman, Kolkata (IN); Biswajit Kundu, Kolkata (IN); Swarnali Roy, Kolkata (IN); Raychaudhuri Deblina, Kolkata (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/760,727

(22) PCT Filed: Nov. 5, 2018

(86) PCT No.: PCT/IN2018/050714
§ 371 (c)(1),
(2) Date: Apr. 30, 2020

(87) PCT Pub. No.: WO2019/092739
PCT Pub. Date: May 16, 2019

(65) Prior Publication Data
US 2020/0347062 A1 Nov. 5, 2020

(30) Foreign Application Priority Data
Nov. 8, 2017 (IN) .............................. 201711039774

(51) Int. Cl.
*C07D 473/16* (2006.01)

(52) U.S. Cl.
CPC ................ *C07D 473/16* (2013.01)

(58) Field of Classification Search
CPC .................................................. C07D 473/16
See application file for complete search history.

(56) References Cited

U.S. PATENT DOCUMENTS

| 6,221,882 B1 | 4/2001 | Macfarlane |
| 6,479,504 B1 | 11/2002 | Macfarlane et al. |
| 7,410,975 B2 | 8/2008 | Lipford et al. |

FOREIGN PATENT DOCUMENTS

| WO | 2012167053 A1 | 12/2012 |
| WO | 2017163264 A1 | 9/2017 |

OTHER PUBLICATIONS

Alexopoulou et al., "Recognition of double-stranded RNA and activation of NF-kB by Tool-like receptor 3", Nature, vol. 413, Oct. 18, 2001.
Bamboat et al., "Toll-Like Receptor 9 Inhibition Confers Protection from Liver Ischemia-Reperfusion Injury", Hepatology, pp. 621-632, Feb. 2010.
Barrat et al., "Treatment of lupus-prone mice with a dual inhibitor of TLR7 and TLR9 leads to reduction of autoantibody production and melioration of disease symptoms", Eur. J. Immunol. vol. 37, pp. 3582-3586, 2007.
Barton et al., "Intracellular localization of Toll-like receptor 9 prevents recognition of self DNA but facilitates access to viral DNA", Nature Immunology, vol. 7, No. 1, Jan. 2006.
Calcaterra et al., "Critical Role of TLR9 in Acute Graft-versus-Host Disease", The Journal of Immunology, vol. 1818, pp. 6132-6139, 2008.
Ganguly et al., "Self-RNA-antimicrobial peptide complexes activate human dendritic cells through TLR7 and TLR8", Journal of Experimental Medicine, pp. 1983-1994, Aug. 24, 2009.
Ganguly et al., "The role of dendritic cells in autoimmunity", Nature Review Immunology, Advance Online Publication, DOI:10.1038/NR13477, Jul. 5, 2013.
Heil et al., "Species-Specific Recognition of Single-Stranded RNA via Toll-like Receptor 7 and 8", Science, vol. 303, pp. 1526-1529, Mar. 5, 2004.
Hemmi et al., "A Toll-like receptor recognizes bacterial DNA", Nature, vol. 408, pp. 740-745, Dec. 7, 2000.
Hoque et al., "TLR9 and the NLRP3 Inflammasome Link Acinar Cell Death With Inflammation in Acute Pancreatitis", Gastroenterology, vol. 141, pp. 358-369, 2011.
Itagaki et al., "Bacterial DNA Induces Pulmonary Damage Via TLR-9 Through Cross-Talk with Neutrophils", Shock, vol. 36, No. 6, pp. 548-552, 2011.

(Continued)

Primary Examiner — Rebecca L Anderson
(74) Attorney, Agent, or Firm — Dinsmore & Shohl LLP

(57) ABSTRACT

The present invention provides novel purine based compounds of formula 1, method of preparation of purine based compounds and its composition useful for inhibiting signalling through Toll-like receptors. These compounds are useful in inhibiting immune stimulation involving toll-like receptor 9 (TLR9). These can be used in treatment of autoimmune disease and inflammation where aberrant activation of TLR9 plays role.

Formula (I)

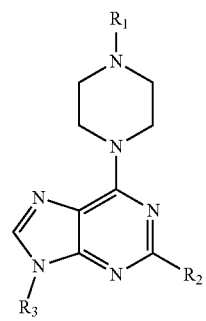

14 Claims, 3 Drawing Sheets

(56) References Cited

OTHER PUBLICATIONS

Lande et al., "Plasmacytoid dendritic cells sense self-DNA coupled with anticicrobial peptide", Nature, vol. 449, pp. 564-571, Oct. 4, 2007.

Lande et al., "Neutrophils Activate Plasmacytoid Dendritic Cells by Releasing Self-DNA-Peptide Complexes in Systemic Lupus Erythematosus", Science Translational Medicine, vol. 3, Issue 73, pp. 1-11, Mar. 9, 2011.

Leadbetter et al., "Chromatin-IgG complexes activate B cells by dual engagement of IgM and Toll-like receptors", Nature, vol. 416, pp. 603-607, Apr. 11, 2002.

Lund et al., "Recognition of single-stranced RNA viruses by Toll-like receptor 7", PNAS, vol. 101, No. 15, pp. 5598-5603, Apr. 13, 2004.

Marshak-Rothstein, "Toll-like receptors in systemic autoimmune disease", Naqture Reviews/Immunology, vol. 6, pp. 823-835, Nov. 2006.

Medzhitov et al., "A human homologue of the *Drosophila* Toll protein signals activation of adaptive immunity", Nature, vol. 388, pp. 394-397, Jul. 24, 1997.

Medzhitov, "Toll-like Receptors and Innate Immunity", Nature, vol. 1, pp. 135-145, Nov. 2001.

Takeda et al., "Toll-Like Receptors", Annu. Rev. Immunol, vol. 21, pp. 335-376, 2003.

Search Report and Written Opinion pertaining to PCT/IN2018/050714 dated Jan. 30, 2019.

PURINE BASED COMPOUNDS AS TOLL-LIKE RECEPTOR 9 ANTAGONIST

FIELD OF THE INVENTION

The present invention relates to the preparation of new compounds with general formula (I) in free form or in pharmaceutically acceptable salts form for inhibiting signalling by TLR9.

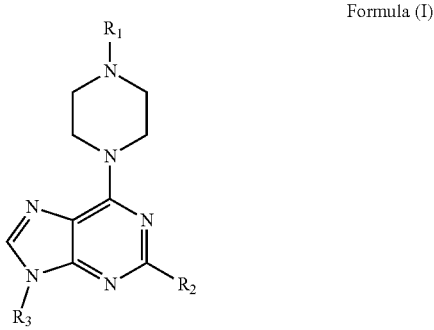

Formula (I)

The invention relates to small molecules where $R_1$, $R_2$, $R_3$, are as defined in the description, capable of inhibiting immune response mediated through TLR9.

The present invention further relates to the preparation of new compounds with general formula (I) without considerable cytotoxicity in HepG2 (a hepatic epithelial cell line) cells at concentrations below 100 μM.

BACKGROUND AND PRIOR ART OF THE INVENTION

The innate immunity is comprised of several types of cells including dendritic cells (DC's), macrophages and monocytes, polymorph nuclear cells, natural killer (NK) cells, innate lymphoid cells and natural killer T cells (NKT cells) which detects various pathogens as well as aberrant host cells with potential for danger to tissue integrity through specialized receptors like toll-like receptors. Toll-like receptors (TLRs) are a family of germline-encoded cell surface pattern recognition molecules containing an pathogen binding ectodomain (ECD) with 19-25 leucine-rich repeats (LRRs), a transmembrane domain and a characteristic cytoplasmic domain called the TIR (Toll/IL-1 receptor) domain. TIR domain is responsible for downstream signalling, whereas LRRs containing 24-29 amino acids are responsible for ligand recognition and binding. TLRs get triggered in response to bacterial and fungal infections (Medzhitov, R; Nat. Rev. Immunol. 1, 135-145, 2001) followed by induction of downstream signalling, leading to expression of inflammatory genes like those of the nuclear factor-κB (NF-κB) family of transcription factors and antimicrobial peptides. There are 11 human and 12 miceTLRs have been identified which recognize different molecular patterns on the pathogens.

Major group of the TLRs are expressed on the cell surface. The leucine-rich repeats in the ectodomains of these molecules bind to unique molecular entities on pathogens (PAMPs), which detect and initiate responses to invading microorganisms (Akira, S; et al. Annu Rev Immunol. 21, 335-76, 2003). Another group of TLRs (endosomal TLRs) are located inside the cell within the endosomal-lysosomal compartments, instead of being expressed on the cell surface (Akira, S; et al. Annu Rev Immunol. 21, 335-76, 2003). This group comprises of TLR3, TLR7, TLR8 and TLR9. The endosomal TLRs are specialized for detecting microbial nucleic acids after microbes get phagocytosed and reach the endosomal compartments.

The downstream signalling goes through recruitment of intracellular adaptor molecules such as Myd88 (or the myeloid differentiation primary-response gene 88), TIRAP (or the TIR-domain containing adaptor protein), TRIF (or the TIRAP inducing IFN-beta) and TRAM (or the TRIF-related adaptor molecule). TLR-adaptor molecule interactions in turn recruit other proteins to the signalling complex, which initiates multiple downstream signalling pathways, leading to activation of NFkB or mitogen-activated protein kinases (MAPKs) or recruitment of the IFN regulatory factors (IRFs). These different pathways in turn result in the transcription of genes encoding different cytokines, chemokines, co-stimulatory molecules or other proteins, thereby sculpting the ensuing immune response (Akira, S; et al. Annu Rev Immunol. 21, 335-76, 2003).

The intracellular localization of the nucleic acid-recognizing TLRs (TLR3, 7, 8, 9) is one of the mechanisms that prevent their spontaneous activation by circulating host-derived nucleic acids (Barton, G. M; et al. Nat Immunol. 7(1):49-56, 2006), however under certain pathological conditions the endogenous nucleic acids can overcome this regulation. It has been previously shown by us and others that the circulating immune complexes found in sera of patients suffering from systemic lupus erythematosus (SLE) typically contain nucleic acids associated with various proteins such as antibodies, the chromatin-associated protein HMGB1, the antimicrobial peptide LL37, ribonuclear proteins and others (Lande, R; et al. Nature, 449(7162), 564-9, 2011; Ganguly, D. et al. Nat Rev Immunol. 13(8), 566-77, 2013). Our previous studies have also shown that TLR9, 7 and 8 activation driven by self nucleic acid and LL37 complexes may also play an important pathogenic role in Psoriasis (Lande, R; et al. Nature, 449(7162), 564-9, 2007; Ganguly, D. et al. J Exp Med. 206(9), 1983-94, 2009). These associated proteins may protect the bound nucleic acid from degradation and/or facilitate their entry into the cell, as is the case for Fc receptor-mediated uptake of antibody-nucleic acid complexes (Ganguly, D. et al. J Exp Med. 206(9), 1983-94, 2009). Once inside the endolysosomal compartments, the nucleic acid cargo can then stimulate the intracellular TLRs, priming the immune system for a cascade of inflammation inciting cytotoxic and/or humoral response. For example, this cycle of innate immune recognition, generation of autoreactive antibodies, and consequent immune complex formation is believed to play critical role in the pathogenesis of SLE and possibly Sjogren's syndrome (Ganguly, D. et al. Nat Rev Immunol. 13(8), 566-77, 2013), a finding confirmed in animal models treated with TLR7 and TLR9-competitive antagonist oligonucleotides (Barrat, F. J; et al. Eur J Immunol. 37(12), 3582-6, 2007). TLR-mediated pathological responses to nucleic acids have also been shown to contribute to other pathologies like psoriasis (Lande R et al, Nature, 2007; Ganguly D et al, J Exp Med, 2009), ischemic liver injury (Bamboat, Z. M; et al. Hepatology, 51(2), 621-32, 2010) lung infection (Itagaki, K; et al. Shock, 36(6), 548-52, 2011), pancreatitis (Hoque, R; et al. Gastroenterology, 141(1), 358-69, 2011) and graft-versus-host disease (Calcaterra, C; et al. J Immunol. 181(9), 6132-9, 2008).

In literature there are several reports of small molecule analogues and derivatives of chloroquine with substituted quinoline and quinazoline scaffold which can inhibit stimulation of the immune system. U.S. Pat. Nos. 6,479,504; 7,410,975 B2.

OBJECTS OF THE INVENTION

The main object of the present invention is to provide novel purine based compounds particularly 6-(piperazin-1-yl)-9H-purin-2-amino compounds and method for preparation thereof.

Another object of the present invention is to provide a screening method involving human peripheral blood mononuclear cells to screen compounds of general formula I against TLR9.

Yet another objective of the present invention is to provide a method for testing TLR9 antagonism of compounds of general formula I, in primary human plasmacytoid dendritic cells (pDCs) purified from human peripheral blood mononuclear cells.

Yet another objective of the present invention is to provide a method for testing TLR9 antagonism of compounds of general formula I a reporter assay method involving a cell line expressing TLR9 to screen compounds of general formula I for TLR9 antagonism.

Yet another objective of the present invention is to correlate the assays results involving human peripheral blood mononuclear cells, human primary pDCs and transfected TLR9 cells.

Yet another object of the present invention is to provide composition and methods of compounds of general formula I with TLR9 antagonistic activity that can modulate immune responses.

Yet another objective of the present invention is to provide composition and methods of compounds of general formula I that can be used in a number of clinical applications, including as pharmaceutical agents and methods for treating conditions involving untoward immune hyperactivity.

Yet another objective of the present invention is to provide composition and methods of compounds of general formula I without considerable cytotoxicity in HepG2 (a hepatic epithelial cell line) and SW480 (an intestinal mucosal epithelial cell line) cells at concentrations below 100 μM.

SUMMARY OF THE INVENTION

Accordingly the present invention provides a compound of formula 1 or salts thereof,

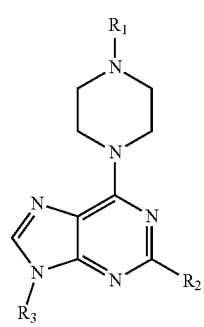

Formula (I)

Wherein
$R_1$ is independently selected from groups referred to as follows:

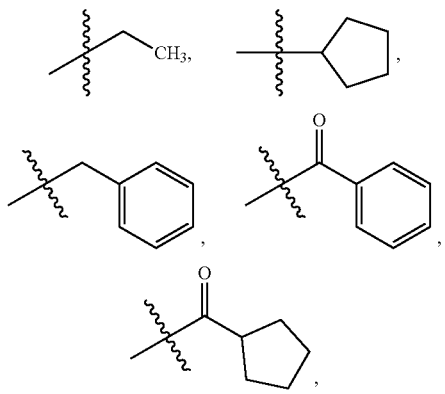

Wherein $R_2$ is independently selected from groups referred to as follows:

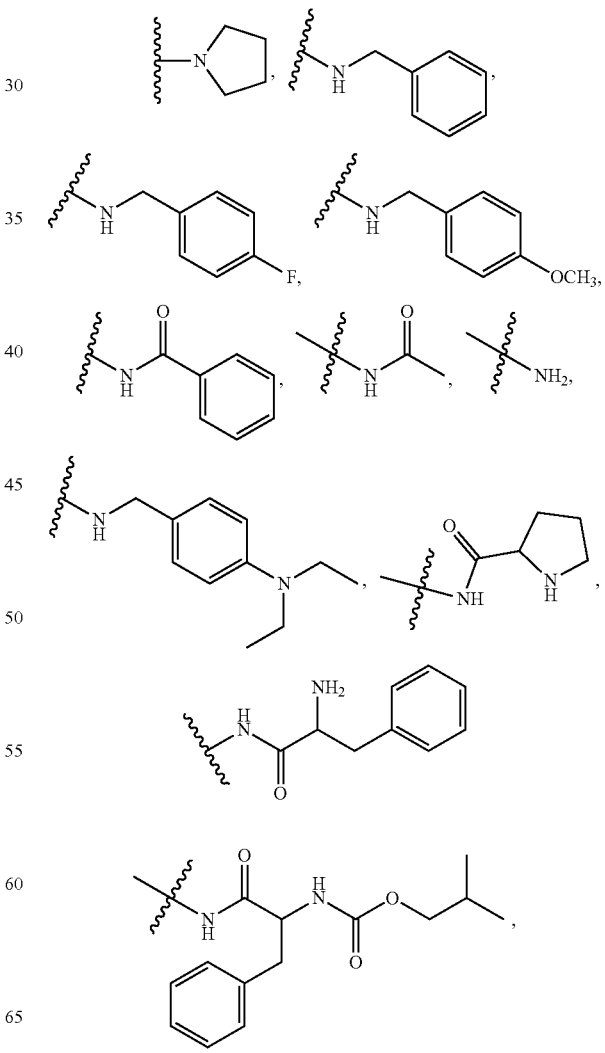

-continued

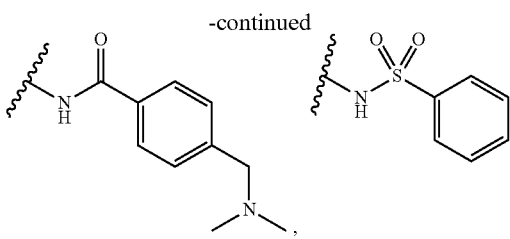

Wherein
R₃ is independently selected from groups referred to as follows:

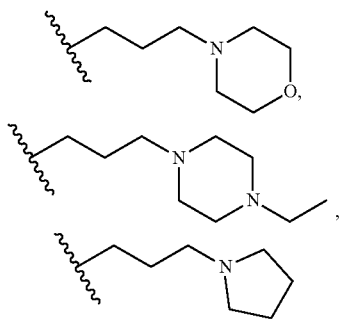

In an embodiment of the invention wherein represented compounds comprising.
6-(4-ethylpiperazin-1-yl)-9-(3-(4-ethylpiperazin-1-yl)propyl)-9H-purin-2-amine (4)
6-(4-ethylpiperazin-1-yl)-9-(3-(4-ethylpiperazin-1-yl)propyl)-N-(4-methoxybenzyl)-9H-purin-2-amine (5)
6-(4-ethylpiperazin-1-yl)-9-(3-(4-ethylpiperazin-1-yl)propyl)-N-(4-fluorobenzyl)-9H-purin-2-amine (6)
N-(4-(diethylamino)benzyl)-6-(4-ethylpiperazin-1-yl)-9-(3-(4-ethylpiperazin-1-yl)propyl)-9H-purin-2-amine (7)
N-benzyl-6-(4-ethylpiperazin-1-yl)-9-(3-(4-ethylpiperazin-1-yl)propyl)-9H-purin-2-amine (8)
6-(4-ethylpiperazin-1-yl)-9-(3-(4-ethylpiperazin-1-yl)propyl-2-(pyrrolidin-1-yl)-9H-purine (9)
N-(6-(4-ethylpiperazin-1-yl)-9-(3-(4-ethylpiperazin-1-yl)propyl)-9H-purin-2-yl)benzamide (10)
Tert-butyl-2-((6-(4-ethylpiperazin-1-yl)-9-(3-(4-ethylpiperazin-1-yl)propyl)-9H-purin-2-yl) carbamoyl)pyrrolidine-1-carboxylate (11)
N-(6-(4-ethylpiperazin-1-yl)-9-(3-(4-ethylpiperazin-1-yl)propyl)-9H-purin-2-yl) pyrrolidine-2-carboxamide (12)
N-(6-(4-ethylpiperazin-1-yl)-9-(3-(4-ethylpiperazin-1-yl)propyl)-9H-purin-2-yl) benzenesulfonamide (13)
N-(6-(4-ethylpiperazin-1-yl)-9-(3-(4-ethylpiperazin-1-yl)propyl)-9H-purin-2-yl)acetamide (14)
Iso-butyl(1-(6-(4-ethylpiperazin-1-yl)-9-(3-(4-ethylpiperazin-1-yl)propyl)-9H-purin-2-yl)amino)-1-oxo-3-phenylpropan-2-yl)carbamate (15)
4-((dimethylamino)methyl)-N-(6-(4-ethylpiperazin-1-yl)-9-(3-(4-ethylpiperazin-1-yl)propyl)-9H-purin-2-yl)benzamide (16)
(4-(2-amino-9-(3-(4-ethylpiperazin-1-yl)propyl)-9H-purin-6-yl)piperazin-1-yl)(phenyl)methanone (18)
4-(2-((4-(diethylamino)benzyl)amino-9-(3-(4-ethylpiperazin-1-yl)propyl)-9H-purine-6-yl)piperazin-1-yl)(phenyl)methanone (19)
(4-(9-(3-(4-ethylpiperazin-1-yl)propyl)-2-(pyrrolidin-1-yl)-9H-purin-6-yl)piperazin-1-yl)(phenyl)methanone (20)
(4-(9-(3-(4-ethylpiperazin-1-yl)propyl)-2-((4-methoxybenzyl)amino)-9H-purin-6-yl)piperazin-1-yl)(phenyl)methanone (21)
(4-(9-(3-(4-ethylpiperazin-1-yl)propyl)-2-((4-fluorobenzyl)amino)-9H-purin-6-yl)piperazin-1-yl)(phenyl)methanone (22)
6-(4-cyclopentylpiperazin-1-yl)-9-(3-(4-ethylpiperazin-1-yl)propyl)-9H-purin-2-amine (23)
6-(4-cyclopentylpiperazin-1-yl)-N-(4-diethylamino)benzyl)-9-(3-(4-ethylpiperazine-1-yl)propyl)-9H-purine-2-amine (24)
6-(4-cyclopentylpiperazin-1-yl)-9-(3-(4-ethylpiperazin-1-yl)propyl)-N-(4-fluorobenzyl)-9H-purin-2-amine (25)
6-(4-cyclopentylpiperazin-1-yl)-9-(3-(4-ethylpiperazin-1-yl)propyl)-N-(4-methoxybenzyl)-9H-purin-2-amine (26)
N-(6-(4-cyclopentylpiperazin-1-yl)-9-(3-(4-ethylpiperazin-1-yl)propyl)-9H-purin-2-yl)-4-((dimethylamino)methyl) benzamide (27)
6-(4-cyclopentylpiperazin-1-yl)-9-(3-(pyrrolidin-1-yl)propyl)-9H-purin-2-amine (29)
6-(4-cyclopentylpiperazin-1-yl)-N-(4-methoxybenzyl)-9-(3-(pyrrolidin-1-yl)propyl)-9H-purin-2-amine (30)
N-(6-(4-cyclopentylpiperazin-1-yl)-9-(3-(pyrrolidin-1-yl)propyl)-9H-purin-2-yl)-4-((dimethylamino)methyl)benzamide (31)
6-(4-cyclopentylpiperazin-1-yl)-N-(4-fluorobenzyl)-9-(3-(pyrrolidin-1-yl)propyl)-9H-purin-2-amine (32)
6-(4-ethylpiperazin-1-yl)-9-(3-(pyrrolidin-1-yl)propyl)-9H-purin-2-amine (33)
6-(4-ethylpiperazin-1-yl)-N-(4-methoxybenzyl)-9-(3-(pyrrolidin-1-yl)propyl)-9H-purin-2-amine (34) 4-((dimethylamino)methyl)-N-(6-(4-ethylpiperazin-1-yl)-9-(3-(pyrrolidin-1-yl)propyl)-9H-purin-2-yl)benzamide (35)
6-(4-ethylpiperazin-1-yl)-N-(4-fluorobenzyl)-9-(3-(pyrrolidin-1-yl)propyl)-9H-purin-2-amine (36)
(4-(2-Amino-9-(3-(4-ethylpiperazin-1-yl)propyl)-9H-purin-6-yl)piperazin-1-yl)(cyclopentyl)methanone (37)
Cyclopentyl(4-(2-(4-(diethylamino)benzylamino)-9-(3-(4-ethylpiperazin-1-yl)propyl)-9H-purin-6-yl)piperazin-1-yl)methanone (38)
Cyclopentyl(4-(9-(3-(4-ethylpiperazin-1-yl)propyl)-2-(4-methoxybenzylamino)-9H-purin-6-yl)piperazin-1-yl) methanone (39)
Cyclopentyl(4-(9-(3-(4-ethylpiperazin-1-yl)propyl)-2-((4-fluorobenzyl)amino)-9H-purin-6-yl)piperazin-1-yl) methanone (40).

In another embodiment of the invention wherein compounds may be in a free form or in pharmaceutically acceptable form.

In another embodiment of the invention wherein compounds may be useful in treating various auto-immune diseases where activation of TLR9 plays a role.

In another embodiment of the invention wherein compounds may be useful in inhibiting TLR9 mediated immune-stimulatory signalling comprising contacting a cell expressing a TLR9 with effective amount of these compounds.

In another embodiment of the invention wherein compounds are prepared by the process wherein the process steps comprising:
(i) reacting 6-chloro-9H-purin-2-amine with ethyl piperazine or 1-(3-chloropropyl)-4-ethylpiperazine in presence of a base in a solvent at reflux temperature for a period ranging between 3 to 4 hrs to obtain compound 2 or 17,
(ii) reacting compound 2 with 1-bromo-3-chloro propane in presence of a base in DMSO, DMF at a room temperature for a period ranging between 10 to 12 hr to obtain compound of formula 3, (iii) reacting compound 3 with ethyl piperazine or pyrrolidine in presence of a base DIPEA or Et$_3$N in a solvent to obtain compound 4 or compound 33 respectively.

(iv) reacting compound 4 as obtained in step (iii) with a compound selected from a group consisting of aromatic aldehyde, acid, acid chloride, dibromoalkane in presence of a base and a solvent at a temperature range between 25 to 110° C., for a period 3 to 24 hr to obtain compound 5 to 16, (v) reacting compound 1 or 17 with a compound phenyl (piperazine-1-yl) methanone, 1-cyclopentylpiperazine or cyclopentyl(piperazin-1-yl)methanone in presence of a base selected form a group comprising of Cs$_2$CO$_3$, K$_2$CO$_3$ solvent selected from THF, dioxane, CH$_3$CN at a temperature ranging between 80 to 100° C. to obtain compound 18, 23, 28 or 37, (vi) reacting compound 18 or 23 with a compound selected from a group consisting of aldehyde, acid or dibromo alkane in a solvent and in the presence of a base at a temperature ranging between 80 to 110° C. for a period ranging between 12 to 24 hr to obtain compound 19 to 22, 24 to 27, (vii) reacting compound 28 with a compound 1-(3-chloropropyl)pyrrolidine to give compound 29, (viii) reacting compound 29, 33 or 37 with a compound of aldehyde or an acid in presence of a solvent and a base, at a temperature ranging between 25 to 100° C., for a period ranging between 3 hr to 24 hr to obtain compound 30 to 32, 34 to 36 and 37 to 40.

In another embodiment of the invention wherein base used in step (i) and step (ii) is selected from a group consisting of Cs$_2$CO$_3$, K$_2$CO$_3$.

In yet another embodiment of the invention wherein solvent used in step (i) is selected from a group consisting of acetonitrile, THF, dioxane, DMF.

In another embodiment of the invention wherein where solvent in step (iii) is selected from a group consisting of toluene, DCM.

In one more embodiment of the invention wherein aromatic aldehyde, acid, acid chloride, dibromoalkane in step (iv), (vi) and (viii) is selected from a group consisting of benzaldehyde, p-anisaldehyde, 4-fluorobenzaldehyde, 4-diethylamino benzaldehyde, benzoyl chloride, 1-(Tert-butoxycarbonyl) pyrrolidine-2-carboxylic acid, benzenesulphonyl chloride, acetyl chloride, 2-(Isobutoxycarbonyl)amino)-3-phenyl propionic acid and dibromopropane 4-[(Dimethyl amino) methyl] benzaldehyde, 1, 4-dibrobutane, 4-[(Dimethyl amino) methyl] benzoic acid.

In another embodiment of the invention wherein base and reducing agent in step (iv), (vi) and step (viii) is selected from group consisting of pyridine, sodium hydride, sodium triacetoxy borohydride, sodium cyanoborohydride, sodium borohydride.

In another embodiment of the invention wherein solvent in step (iv), (vi) and (viii) is selected from group consisting of toluene, dichloromethane, THF, DMF.

Further embodiment of the invention wherein the compounds can be used for the preparation of pharmaceutical composition comprising a compound as claimed in claim (I) optionally along with pharmaceutically-acceptable excipients.

In another embodiment according to this aspect of the invention, a screening method is provided to screen compounds of general formula I for testing TLR9 antagonism in primary human plasmacytoid dendritic cells (pDCs) purified from human peripheral blood mononuclear cells.

In another embodiment according to this aspect of the invention, a screening method of affecting TLR mediated signalling in response to a TLR ligand is provided, which involves detecting TLR9 antagonism of effective amount of a compound of general Formula (I) using a reporter cell line that reports nuclear factor kappa B expression downstream of TLR9 signalling.

In another embodiment according to this aspect of the invention, said compounds with formula (I) described by the present invention affect immune response mediated through TLR9.

In another embodiment according to this aspect of the invention, compounds of general formula I described by the present invention inhibit immune stimulation via TLR9 antagonism.

In another embodiment according to this aspect of the invention, compounds of general formula (I) is useful whenever it is desirable to alter TLR9 mediated signalling in response to a suitable TLR ligand or TLR signalling agonist.

In another embodiment according to this aspect of the invention, it is believed that the said compounds with formula (I) can be useful to inhibit an immune stimulatory nucleic acid associated response in a subject.

In another embodiment according to this aspect of the invention, it is believed that the said compounds with general formula (I) that can modulate autoreactive inflammation in different autoimmune diseases where aberrant TLR9 activation is implicated for such diseases.

In another embodiment according to this aspect of the invention, it is believed that the said compounds with general formula (I) can be used in a number of clinical applications, including as pharmaceutical agents and methods for treating conditions involving unwanted immune activity due to TLR9 activation.

In another embodiment according to this aspect of the invention, the said compounds with formula (I) is believed to affect TLR9 directly and thus affect TLR-bearing cells, such as antigen-presenting cells (APCs).

in the presence of different doses of the antagonist molecules. Each data is derived from two donors. Average values are reported.

Figure 4:
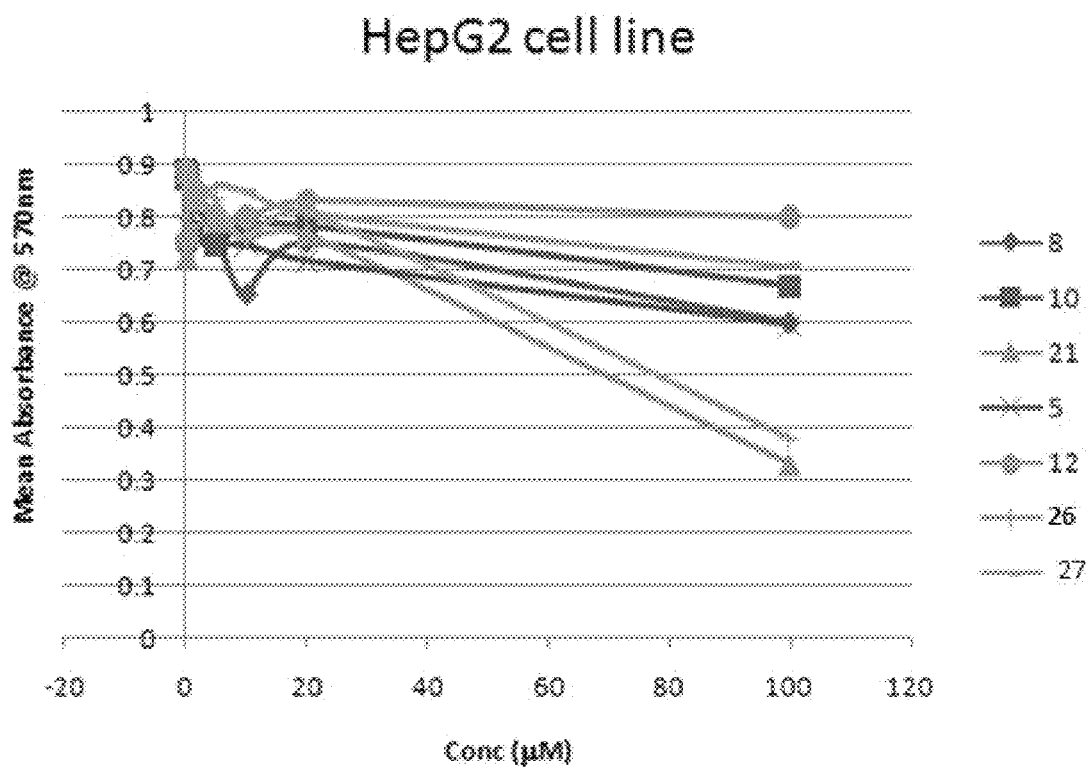

FIG. 4: Cytotoxicity based on MTT assay of the identified TLR9 antagonist molecules with general formula (I). HepG2 and SW480 cells were cultured in presence of different concentrations (0.1, 0.5, 1, 10, 20 and 100 µM) of different compound with general formula (I) for 24 hrs. At 24 hrs MTT assay was performed as described in the text. Respective absorbance at 570 nm is represented. Each line represents a specific small molecule as denoted in the legend.

Table 1 depicts overall structure of the compounds with general formula (I) composition of the Invention Table 2 depicts IC50 values of the compounds with general formula (I) composition of the Invention.

ABBREVIATIONS

BnBr Benzylbromide
DMF N,N-dimethylformamide
AcOH Acetic acid
CDI 1,1'-Carbonyldiimidazole
POCl$_3$ phosphorous oxychloride
DIPEA N,N-Diisopropylethylamine
DCM Dichloromethane
TFA Trifluoroacetic acid
DMSO Dimethyl sulfoxide
Boc Tert butyl carbamate
THF Tetrahydrofuran
HATU 1-[Bis(dimethylamino)methylene]-1H-1,2,3-triazolo[4,5-b]pyridinium-3-oxide hexafluorophosphate

DETAILED DESCRIPTION OF THE INVENTION

The Present Invention is Described Here in Detail for Making and Using the Compounds of Formula I Compound 2 was prepared by using 6-chloro-9H-purin-2-amine and ethylpiperazine as starting materials and potassium carbonate as a base, in acetonitrile at reflux for 3-4 h. Compound 2 was treated with 1-bromo-3-chloro propane in the presence of K$_2$CO$_3$ as a base, in DMF at room temperature for 12 h to give compound 3. Compound 3 was taken in a seal tube treated with the ethylpiperazine and potassium carbonate as a base, in DMSO at 100° C. for 24 hours the residue was separated by the column chromatography to give compound 4. Subsequently, compound 4 was treated with the 4-methoxybenzaldehyde under refluxing condition in presence of the molecular sieves in toluene for 24 hours, thereafter toluene was evaporated and sodium triacetoxyborohydride was added and the reaction mixture was stirred for two hour, residue was separated by column chromatography to get compound 5. Compound 4 was similarly treated with 4-fluorobenzaldehyde under refluxing condition in presence of molecular sieves in toluene for 24 hours. Subsequently sodium triacetoxyborohydride was introduced and the reaction stirred for one hour at room temperature, the residue was separated by the column chromatography to get the compound 6. Compound 4 was treated with benzaldehyde and 4-diethylamino benzaldehyde separately in toluene at reflux for 12 h. After cooling sodium acetoxyborohydride was added and stirred for 12 h at room temperature. The residue was purified by using column chromatography to give compound 8 and 7. Compound 4 was treated with 1,4-dibromobutane in DMF, NaH used as a base at 80° C. and stirred for 24 hours, residue was separated by the column chromatograph, to get compound 9. Compound 4 was treated with benzoyl chloride in the presence of pyridine in DCM for 10 h at room temperature and purified by column chromatography to provide compound 10. 1-(tert-butoxycarbonyl) Pyrrolidine-2-carboxylic acid was treated with oxalyl chloride and catalytic amount of DMF and pyridine in DCM to produce acid chloride in situ and compound 4 was added to this mixture to undergo amide coupling to give compound 11 after column chromatography. Compound 1 was treated with trifluoroacetic acid in DCM at 0° C. for 30 mins and quenched with ammonia and purified by column chromatography to give compound 12. Compound 13 was prepared by treating compound 4 with benzene sulfonyl chloride in presence of pyridine in DCM and DMAP was added at catalytic amount and stirred for 10 h and the residue was purified by column chromatography. Compound 4 was undergone amide coupling with acetyl chloride, in presence of pyridine in DCM. The residue was purified by using column chromatography to give compound 14. 2-(Isobutoxycarbonyl) amino)-3-phenylpropanoic acid was treated with oxalyl chloride and catalytic amount of DMF and pyridine in DCM to produce acid chloride in situ and compound 4 was added to this mixture to undergo amide coupling to give compound 15 after column chromatography purification. Compound 16 was synthesised by treating compound 4 with 4-((dimethylamino)methyl)benzoic acid and POCl$_3$ in pyridine. The residue was purified by column chromatography to give compound 16. Compound 17 was prepared by treating compound 1 with 1-(3-choloropropyl)-4-ethylpiperazine in presence of potassium carbonate as a base in DMF at 120° C. for 24 hours. The residue was separated by column chromatography, to give compound 17, which was treated with phenyl (piperazin-1-yl)methanone and potassium carbonate under refluxing condition, in acetonitrile for 12 hours at 100° C. to give compound 18. Thereafter, compound 18 was treated with 4-diethyl aminobenzaldehyde in toluene under refluxing condition for 24 hours. The solvent was evaporated and sodium triacetoxyborohydride was introduced and the reaction mixture stirred for 2 hours to give the compound 19. Compound 18 was also treated with 1, 4-dibrobutane in DMF, at 60° C. for 12 hours; residue is separated by column chromatography to get the compound 20. Compound 17 was treated with the 1-cyclopentenyl-4-ethylpiperazine, potassium carbonate as a base, in acetonitrile at 100° C. for 12 hours; residue was separated by the column chromatography to give compound 23. Compound 23 was treated with 4-diethyl amino benzaldehyde in toluene at 110° C. for 24 hours and subsequently sodium triacetoxyborohydride was added. The residue was separated by column chromatography to get the compound 24. Compound 23 was treated with 4-fluorobenzaldehyde in toluene at 110° C. for 24 hours and subsequently sodium triacetoxyborohydride was added and stirred at room temperature for 2 hours. The residue was purified by column chromatography to give compound 25. Compound 26 was prepared by treating compound 23 with 4-methoxybenzaldehyde under refluxing condition in presence of the molecular sieves in toluene for 24 hours. Thereafter toluene was evaporated and sodium triacetoxyborohydride was added and the reaction mixture was stirred for two hours in DCE. The residue was purified by column chromatography to give compound 26. Compound 27 was synthesised by treating compound 23 with 4-((dimethylamino)methyl)benzoic acid and POCl$_3$ in pyridine. The residue was purified by column chromatography to give compound 27. Compound 28 was prepared by treating 6-chloro-9H-purin-2-amine with 1-cyclopentylpiperazine and potassium carbonate as a base in acetonitrile at 100° C. for 12 hours. 1-(3-chloropropyl)

pyrrolidine was added to a stirred suspension of compound 28 and potassium carbonate in dry DMF and the reaction mixture was heated for 12 hours at 80° C. to give compound 29. Compound 30 was synthesised by treating compound 29 with 4-methoxybenzaldehyde under refluxing condition in presence of the molecular sieves in toluene for 24 hours. Then toluene was evaporated and sodium triacetoxyborohydride was added and the reaction mixture was stirred for two hours in dichloroethane. The residue was purified by column chromatography to obtain compound 30. Compound 31 was prepared by the reaction of compound 29 and 4-((dimethylamino)methyl)benzoic acid and POCl$_3$ in pyridine. The residue was purified by column chromatography to obtain compound 31. Compound 29 was heated with 4-fluorobenzaldehyde in toluene at 110° C. for 24 hours and subsequently sodium triacetoxyborohydride was added and stirred at room temperature for 2 hours. The residue was purified by column chromatography to get compound 32. Compound 33 was synthesised by heating compound 3 with pyrrolidine and triethylamine as base in DMSO at 110° C. for 24 hours. Compound 34 was prepared by treating compound 33 with 4-methoxybenzaldehyde under refluxing condition in presence of the molecular sieves in toluene for 24 hours. Then toluene was evaporated and sodium triacetoxyborohydride was added and the reaction mixture was stirred for two hours in dichloroethane. The residue was purified by column chromatography to obtain compound 34. Compound 35 was synthesised by reacting compound 33 with 4-(((dimethylamino)methyl)benzoic acid and POCl$_3$ in pyridine. The residue was purified by column chromatography to give compound 35. Compound 36 was prepared by reacting compound 33 with 4-fluorobenzaldehyde in toluene at 110° C. for 24 hours and subsequently sodium triacetoxyborohydride was added and stirred at room temperature for 2 hours. The residue was purified by column chromatography to obtain compound 36. Compound 17 was heated with cyclopentyl(piperazin-1-yl)methanone and potassium carbonate in acetonitrile for 12 hours at 100° C. to give compound 37. Compound 38 was synthesised by reacting compound 37 with 4-(diethylamino)benzaldehyde in toluene at refluxing condition for 24 hours. Toluene was evaporated and sodium triacetoxyborohydride was added in dichloroethane. The residue was purified by column chromatography to obtain compound 38. Compound 39 was prepared by reacting 4-methoxybenzaldehyde under refluxing condition in presence of the molecular sieves in toluene for 24 hours. Toluene was evaporated and sodium triacetoxyborohydride was added and the reaction mixture was stirred for two hours in dichloroethane. The residue was purified by column chromatography to obtain compound 39. Compound 40 was synthesised by reacting with compound and 4-((dimethylamino)methyl)benzoic acid and POCl$_3$ in pyridine. The residue was purified by column chromatography to obtain compound 40.

A screening method was used for evaluating TLR 9 antagonistic activities of the synthesized compounds of general formula (I) by a medium throughput biological assay based on TLR 9 activation in primary human immune cells. The bona fide ligands used for TLR9 activation are Type A and type B unmethylated cytosine-guanine rich DNA oligonucleotides (CpG oligonucleotides).

Type I interferons (e.g. IFN-alpha) are released on activation of TLR9 by CpG oligonucleotides. The synthesized compounds of general formula I was able to alter the release of type I interferons (e.g. IFN-alpha).

Figure 1:
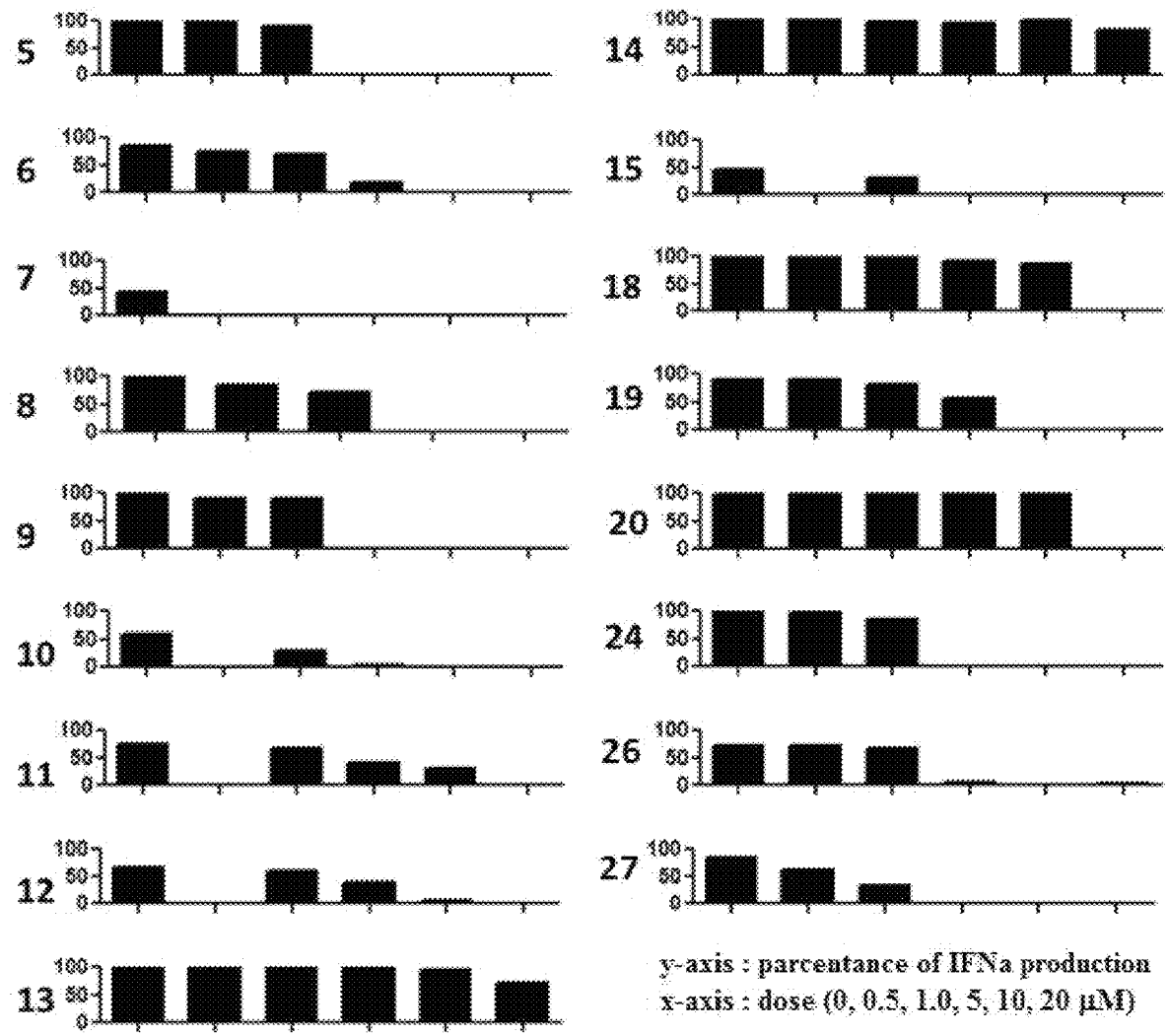
FIG. 1: Structural evolution of the compound with general formula (I) along with respective TLR9-antagonistic activity. The figure denotes percent interferon alpha production in response to TLR9-agonist ODN2216 from human peripheral blood mononuclear cells in the presence of different doses of the compound with general formula (I) (0, 0.1, 1, 5, 10, 20 µM). Each row represents a single molecule with increasing antagonist concentrations from left to right as shown in the figure. TLR9-antagonist activity of one representative molecule belonging to each structural subset is indicated.

The principle of the screening assay was designed based on the production of Type I interferons (IFN-alpha) from human PBMCs, which results almost exclusively from TLR9 triggering on the PDCs by type A CpG oligonucleotides (CpGA). PBMCs were isolated from venous blood collected from healthy donors using density gradient centrifugation. The synthesized compounds of general formula (I) having TLR9 antagonistic activity inhibited IFN-alpha production in this screening assay (FIG. 1).

Figure 2:
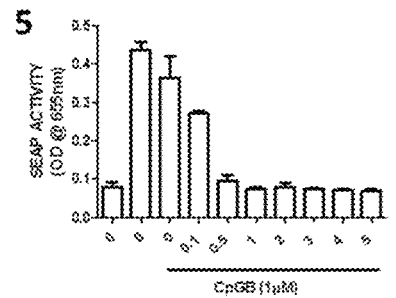
FIG. 2: TLR9 inhibition in HEK-Blue-hTLR9 reporter cell line by selected compounds with general formula (I). The graphs denote dose-dependent inhibition of TLR9 activation in a HEK-Blue-hTLR9 reporter cell line in the presence of different doses of the compound with general formula (I), which is represented in terms of decrease in SEAP activity. Data shown are mean of triplicate wells±SD.
Figure 2:
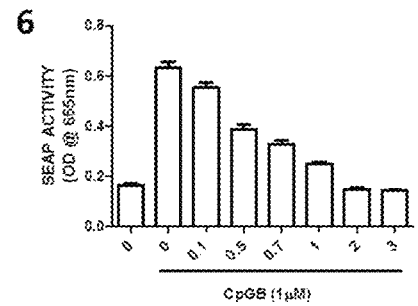
Figure 2:
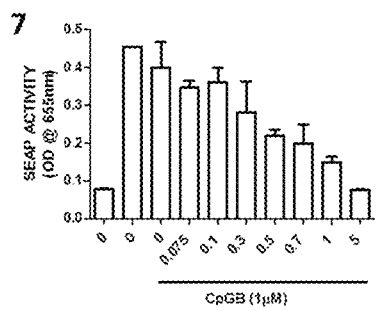
Figure 2:
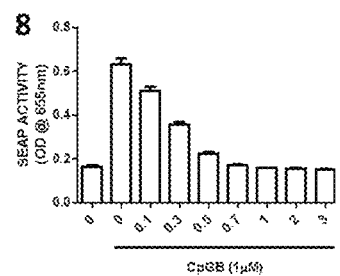
Figure 2:
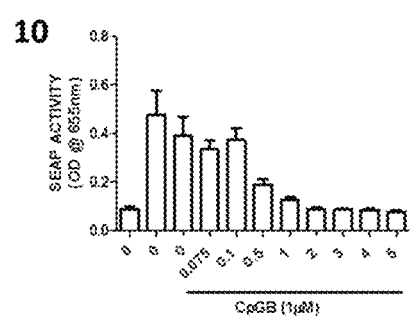
Figure 2:
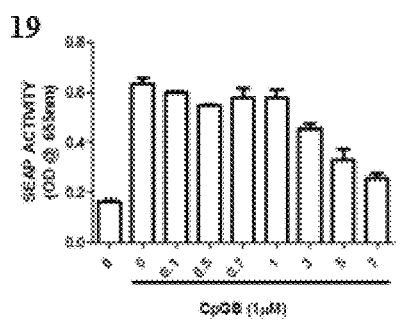
Figure 2:
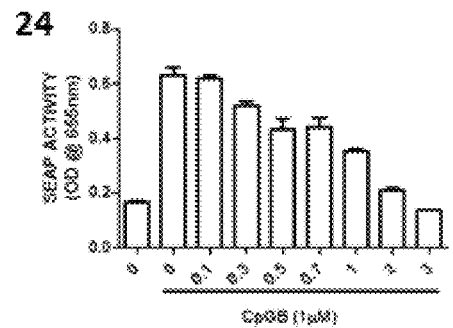

A screening method is provided using a HEK-Blue-hTLR9 Secreted Alkaline Phosphatase (SEAP) reporter assay for the synthesized compounds of general Formula (I) with TLR9 antagonism. The method involves detecting TLR9 antagonistic activity for the synthesized compounds of general Formula (I) by inhibiting TLR9-mediated NF-kB activation in a dose-dependent manner (FIG. 2).

Figure 3:
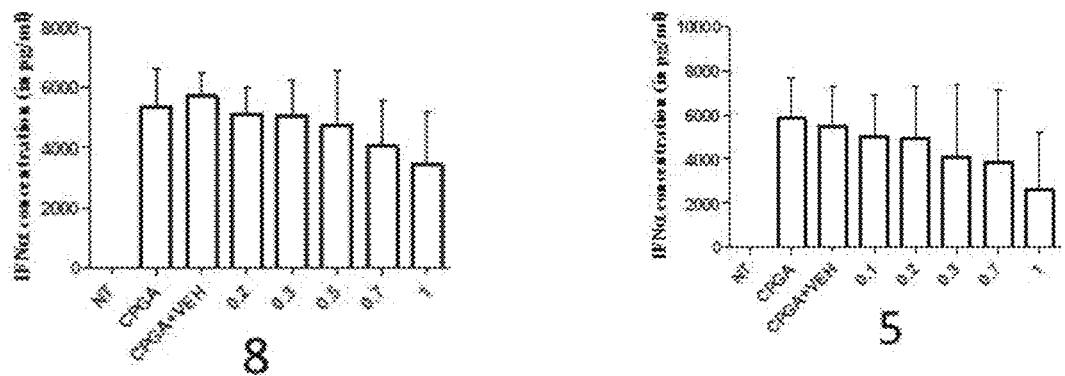
FIG. 3: TLR9 inhibition in pDCs by selected compounds with formula (I). The graphs denote dose-dependent reduction in IFN-α production in response to TLR9-agonist ODN2216 from human plasmacytoid dendritic cells (pDC)

A biological assay based screening method is provided for compounds of general formula (I) for testing TLR9 antagonism in primary human plasmacytoid dendritic cells (pDCs) purified from human peripheral blood mononuclear cells. The assay is based on toll-like receptor 9 activation in pDC (FIG. 3).

MTT assay for assessing cell viability is used to screen for cytotoxicity for the synthesized compounds of general Formula (I). In the cytotoxicity assay PBMC, HepG2 (a hepatic epithelial cell line) and SW480 (an intestinal mucosal epithelial cell line) cells were used. The synthesized compounds of general Formula I did not show any considerable cytotoxicity at concentrations below 100 uM on this assay (FIG. 4).

EXPERIMENTAL DETAILS

The following examples are intended for illustrative purposes only and are not to be construed as being limitations for the invention thereon in any manner. Temperatures are given in degree Celsius. The structure of final products, intermediates and starting materials is confirmed by standard analytical methods, e.g. spectroscopic characterization, e.g., MS, NMR. Abbreviations used are those conventional in the art.

All starting materials, reagents, catalysts, building blocks, acids, bases, dehydrating agent and solvents utilized to synthesize the compounds of the present invention are either commercially available or can be produced by known organic synthesis methods in the art.

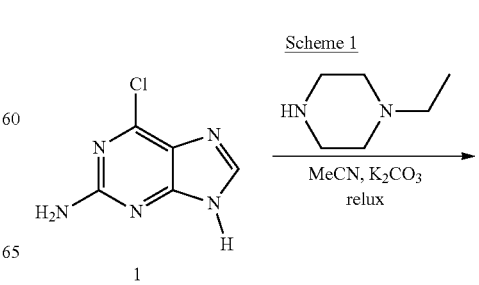

Scheme 1

-continued
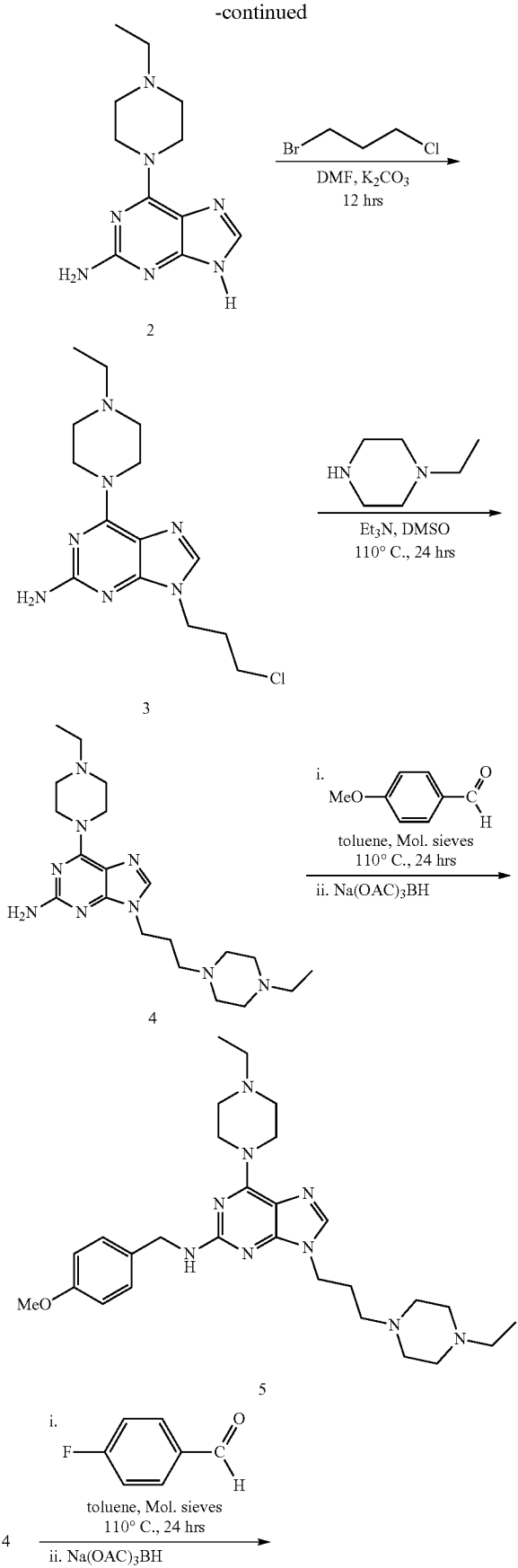
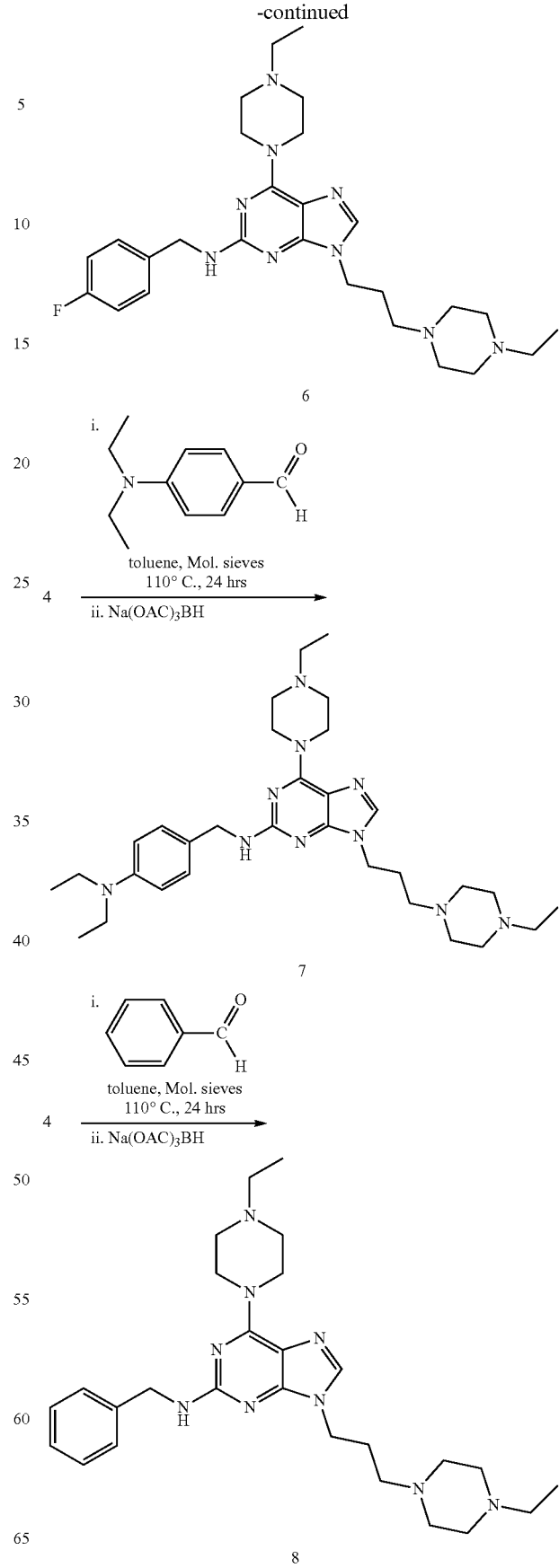

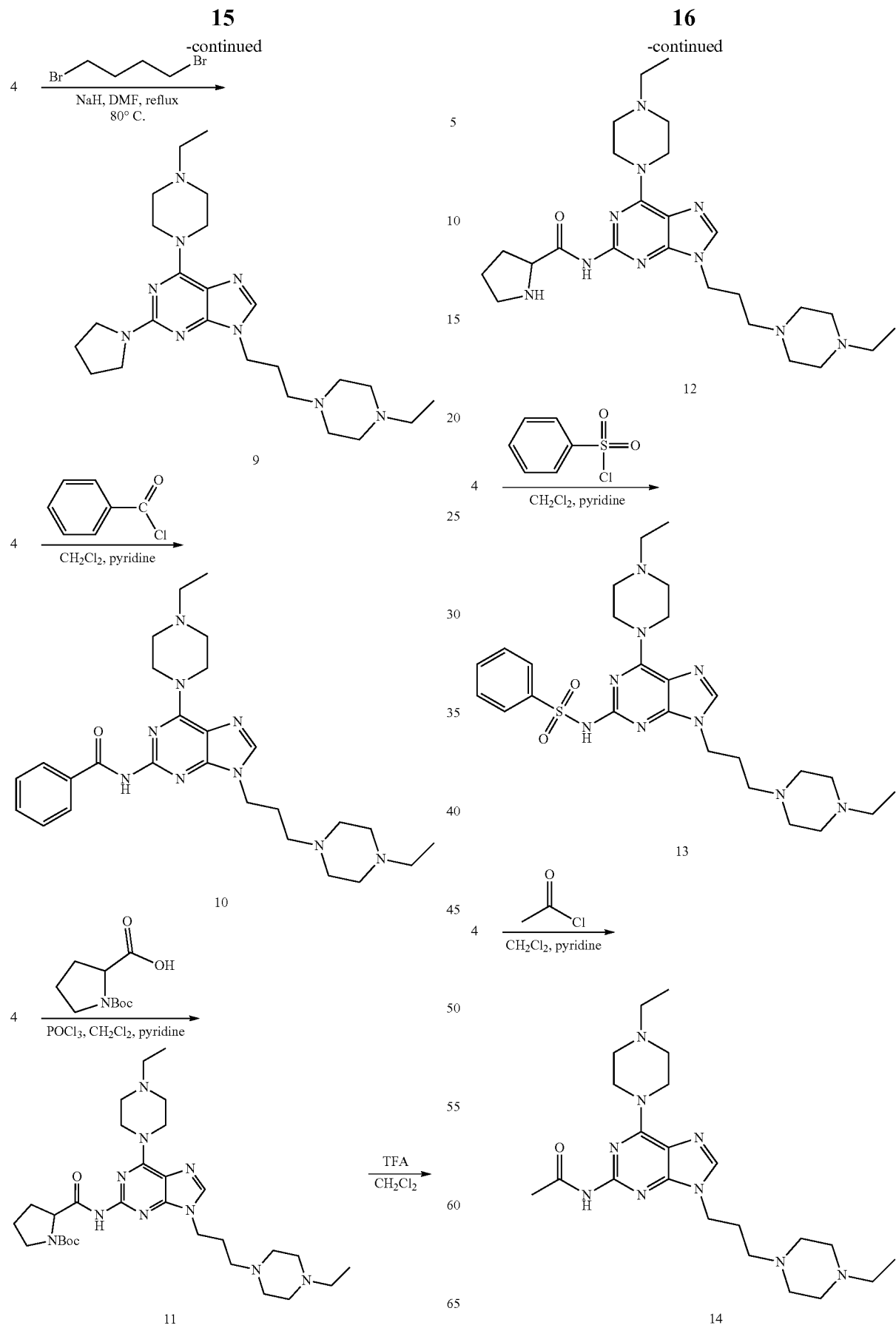

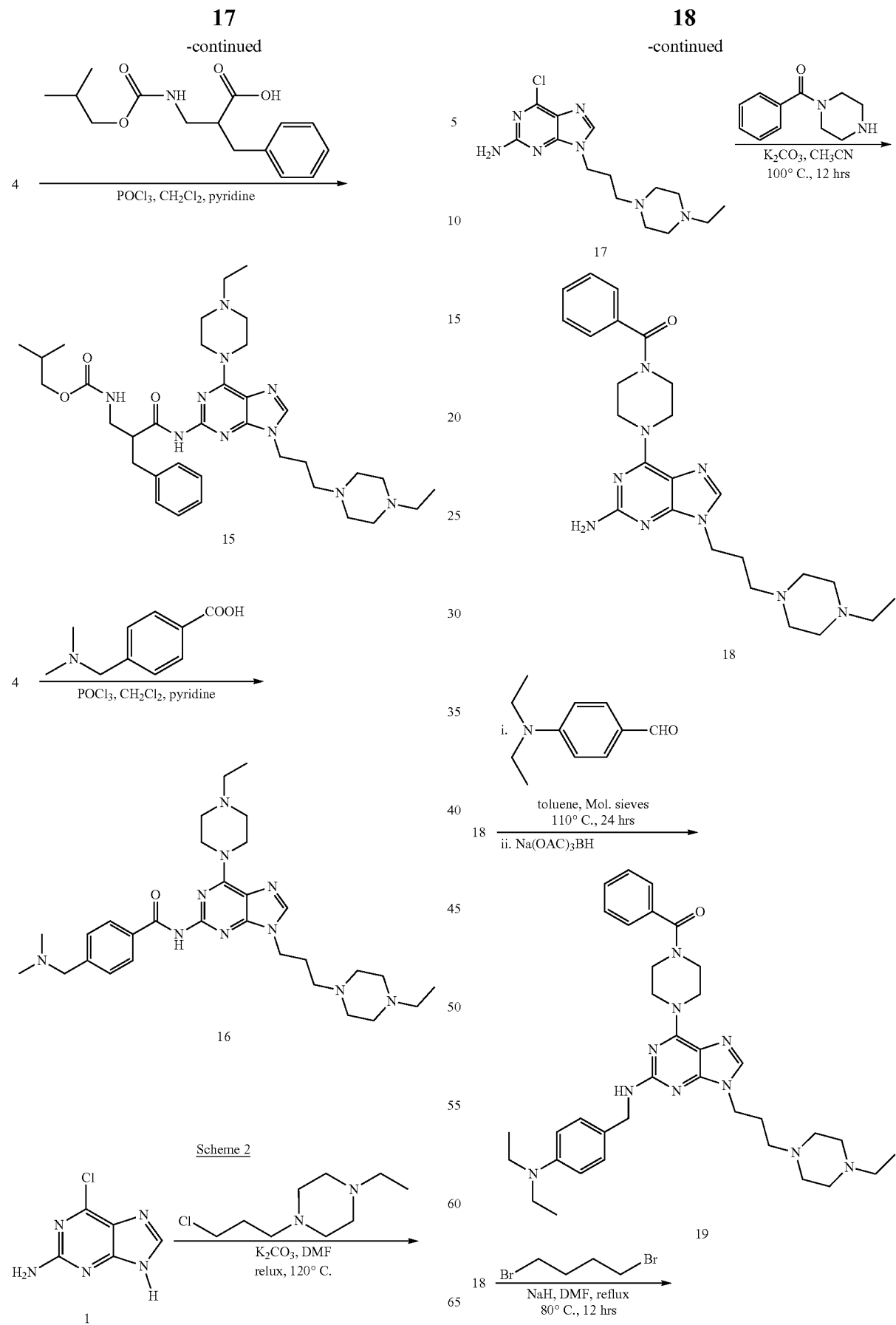

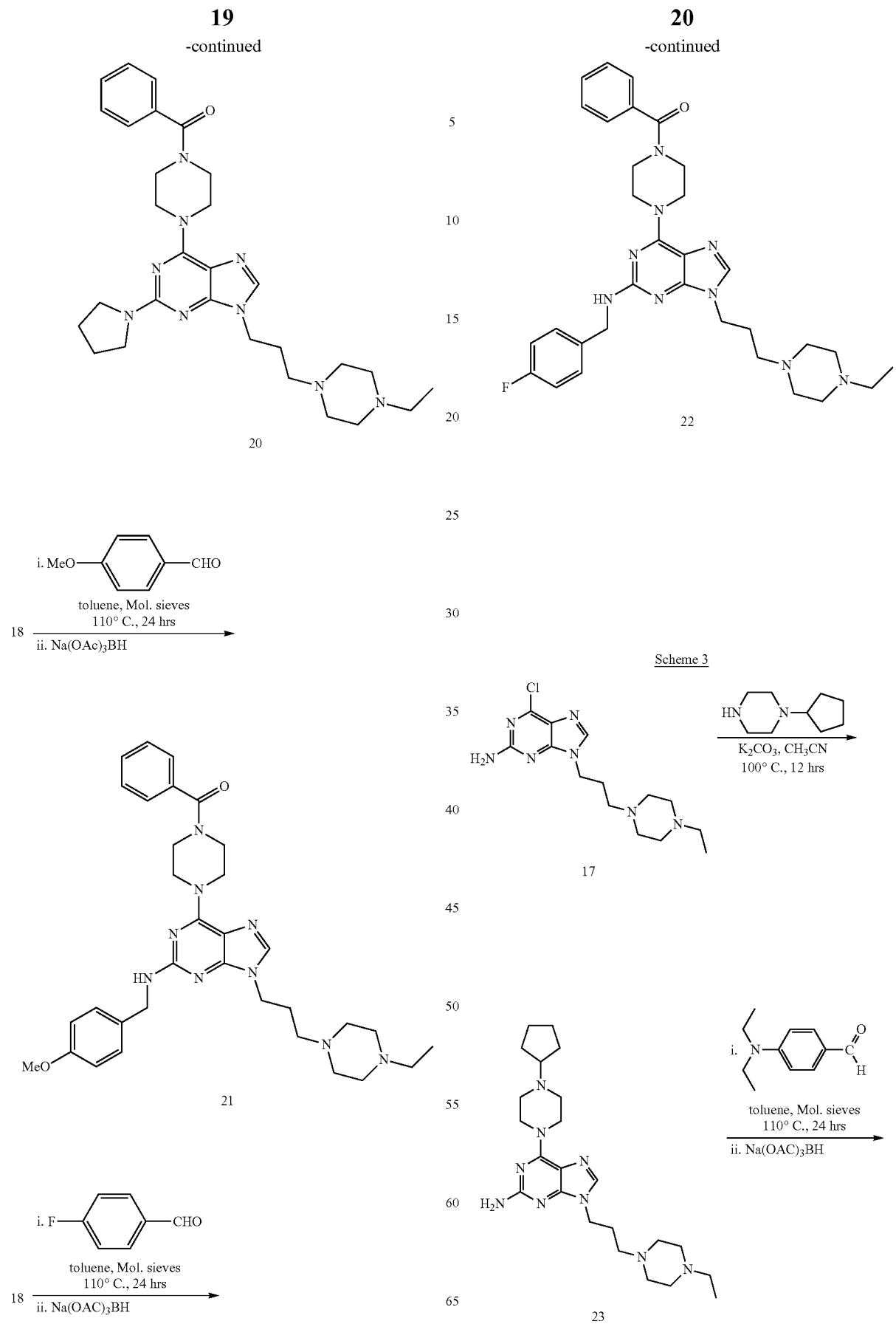

-continued
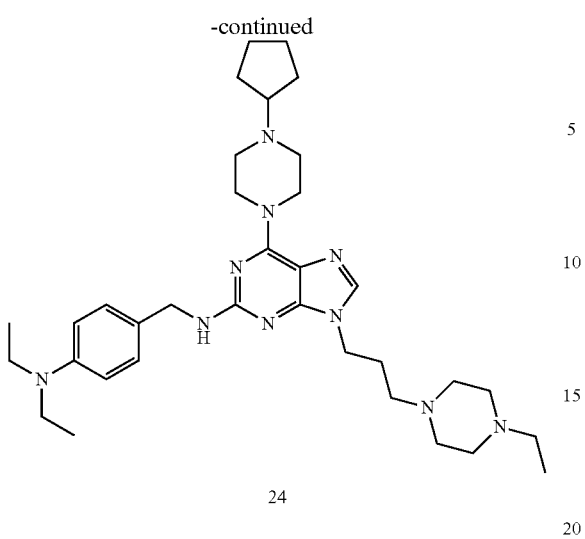
24
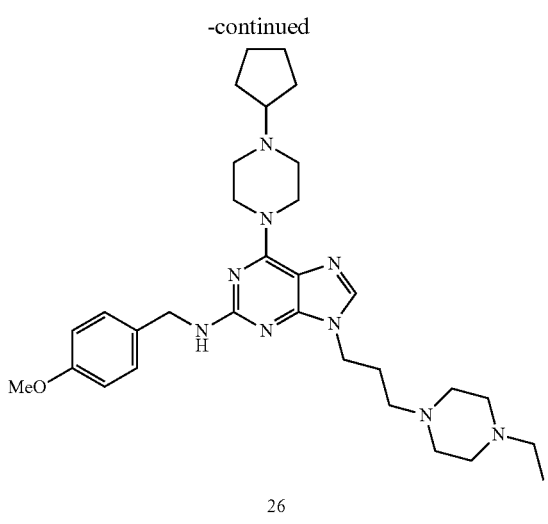
26
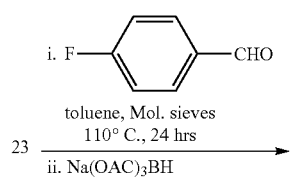
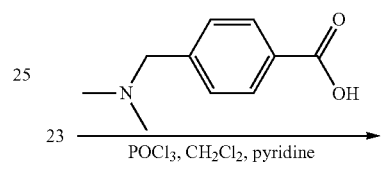
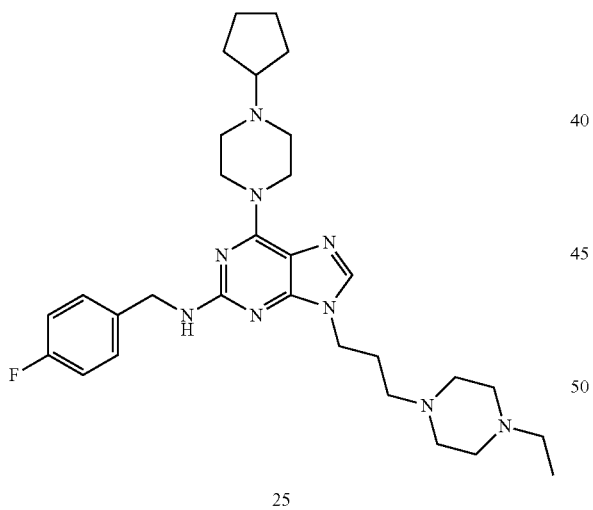
25
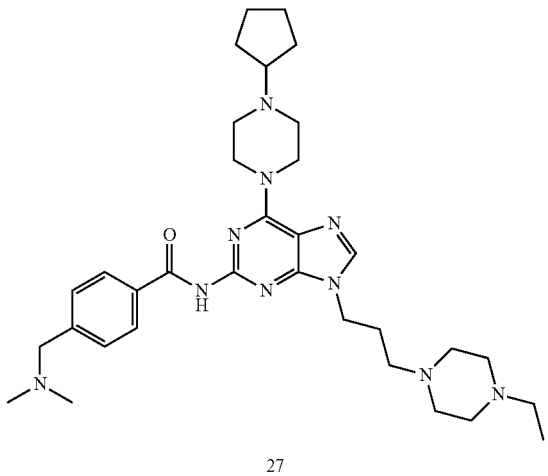 [SMILES: CCN1CCN(CCCn2cnc3c(N4CCN(C5CCCC5)CC4)nc(NC(=O)c4ccc(CN(C)C)cc4)nc32)CC1]
27
Scheme 4
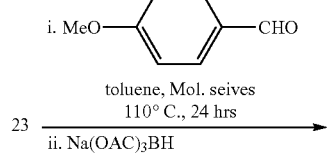
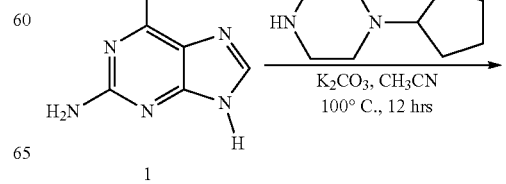

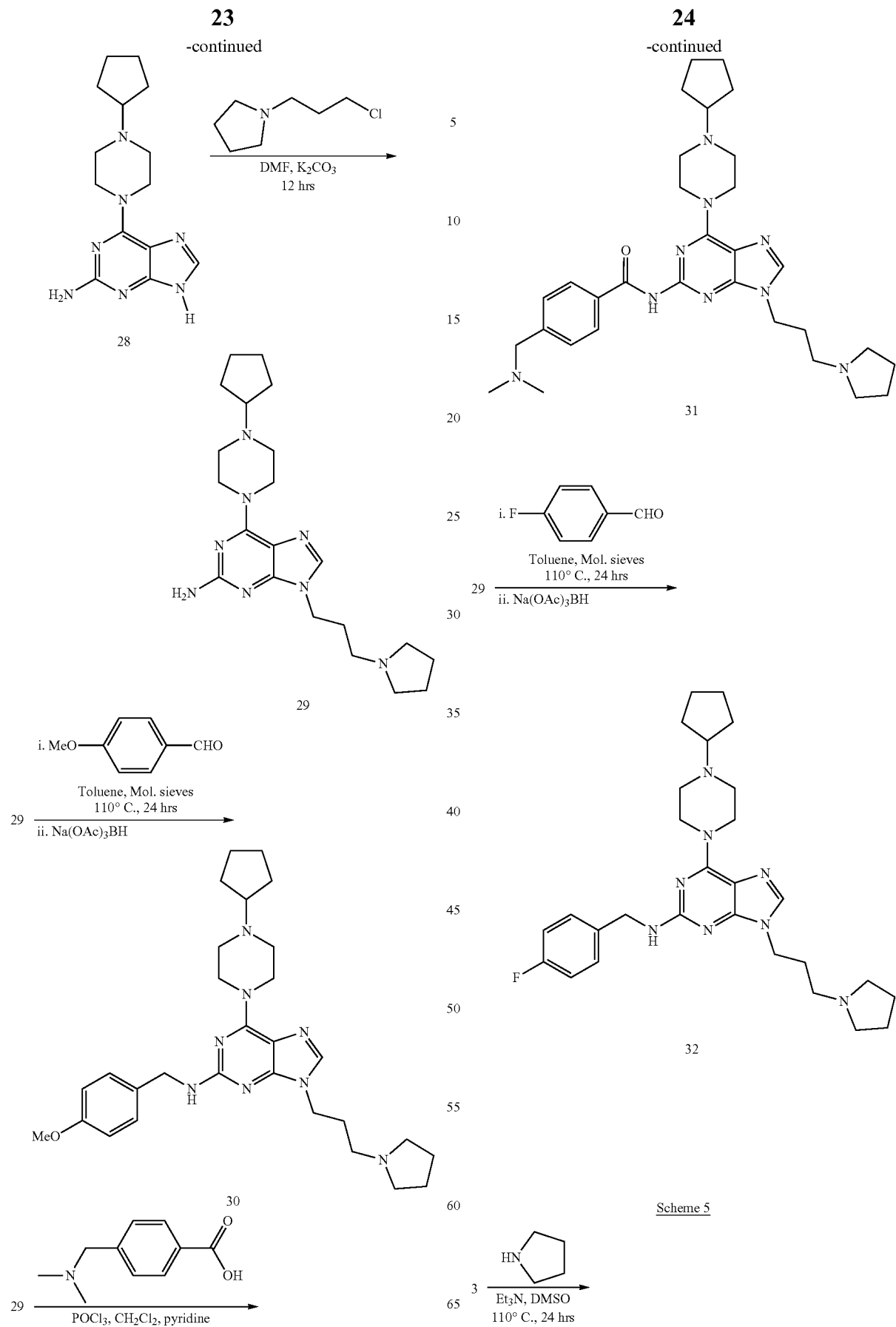

25
-continued
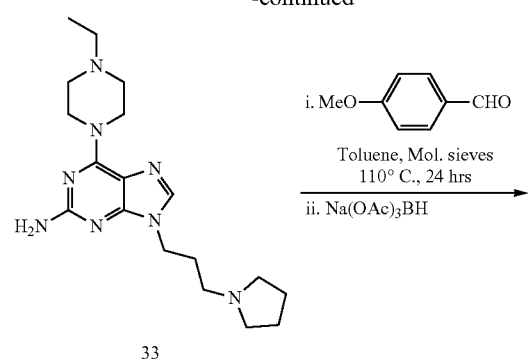
26
-continued
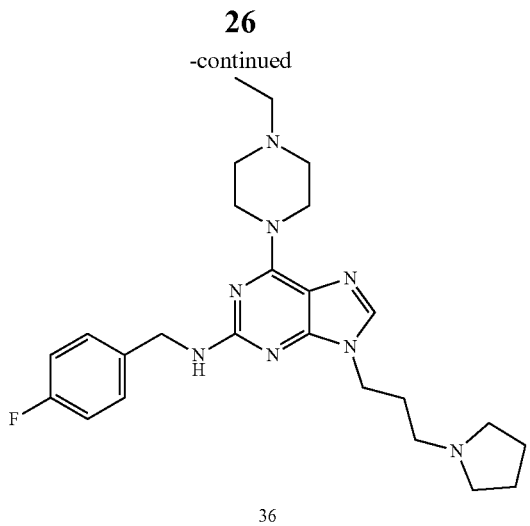
Scheme 6
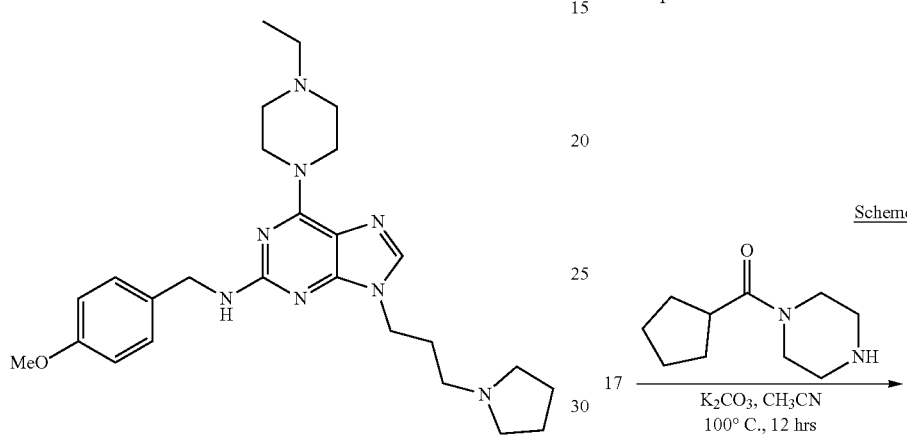
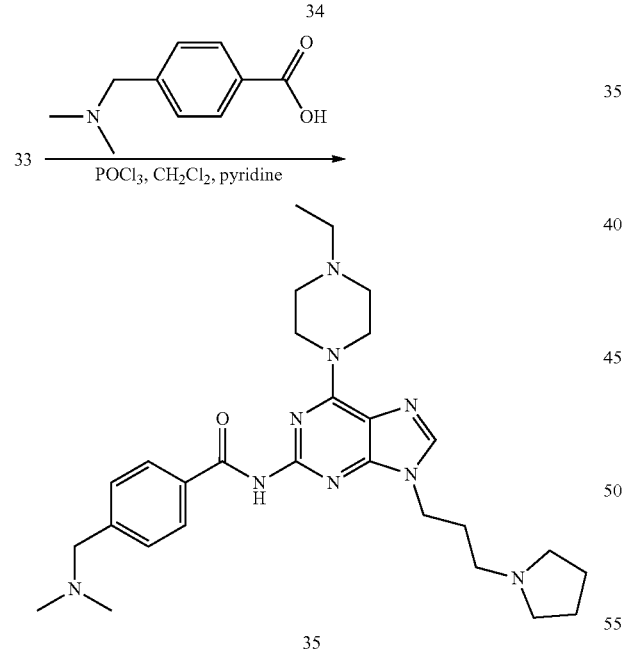

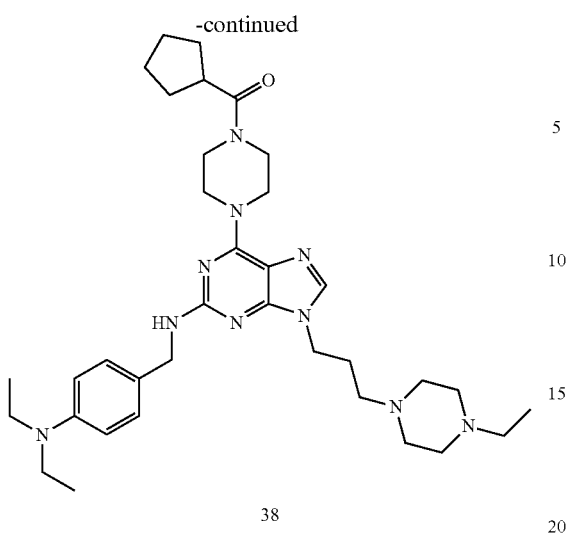

38

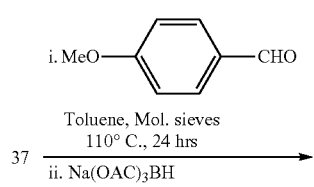

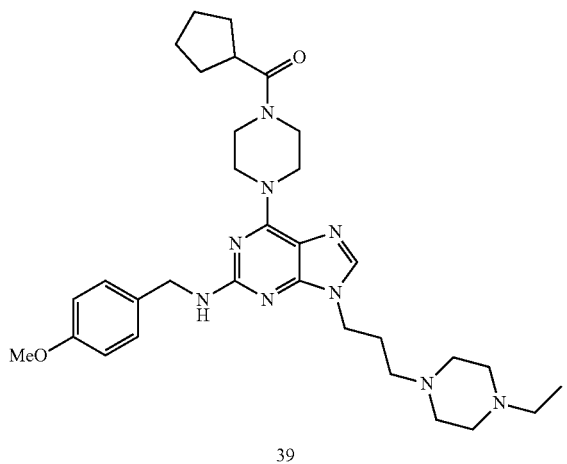

39

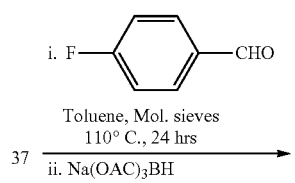

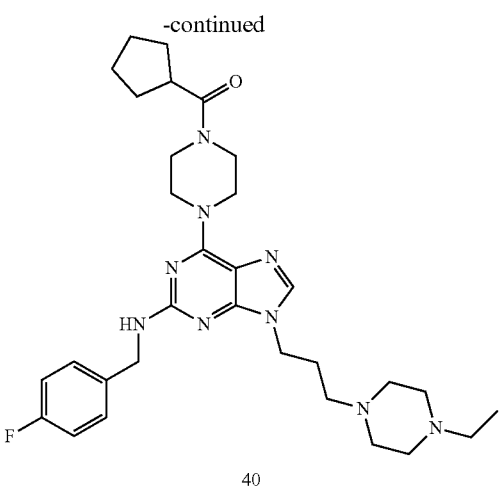

40

Following Examples are Given by Way of Illustration and should not be Construed the Scope of the Invention Example 1

Synthesis of 6-(4-ethylpiperazine-1-yl)-9H-purin-2-amine (2)

1-Ethylpiperazine (1.01 g, 8.84 mmol) was added to a stirred suspension of 6-chloro-9H-purin-2-amine 1 (1 g, 5.89 mmol) and potassium carbonate (0.8 g, 5.89 mmol) in dry acetonitrile. The mixture was heated at reflux for 3-4 hours. acetonitrile was removed under vacuum, the residue then washed with water, followed by filtration and dried to obtain compound 2 as a light brown solid (1.3 g, 89.6%). $^1$H NMR (300 MHz, CDCl$_3$) δ ppm 7.61 (s, 1H), 4.22-4.31 (m, 7H), 2.56-2.63 (m, 4H), 2.50 (q, J=7.1 Hz, H), 1.15 (t, J=7.2 Hz, 3H); ESI-MS m/z 248.20 (M+H).

Synthesis of 9-(3-chloropropyl)-6-(4-ethylpiperazine-1-yl)-9H-purin-2-amine (3)

1-Bromo-3-chloropropane (2.4 mL, 24.26 mmol) was added to a stirred suspension of compound 2 (2 g, 8.08 mmol) and potassium carbonate (1.1 g, 8.08 mmol) in dry DMF and the reaction mixture was stirred for 12 hours at room temperature. Water was added to the reaction mixture. The aqueous solution was extracted with chloroform and the organic layer was dried over Na$_2$SO$_4$ and evaporated under vacuum. The residue was purified by silica gel column chromatography eluting with 5% methanol in chloroform, to provide compound 3 (1.65 g, 63%) as colorless liquid. $^1$H NMR (300 MHz, CDCl$_3$) δ ppm 7.50 (s, 1H), 4.61-4.71 (m, 2H), 4.18-4.36 (m, 6H), 3.50 (t, J=6.1 Hz, 2H), 2.56 (t, J=1.00 Hz, 4H), 2.46 (q, J=7.14 Hz, 2H), 2.31 (q, J=1.00 Hz, 2H), 1.13 (t, J=7.23 Hz, 3H); ESI-MS m/z 324.43 (M+H).

Synthesis of 6-(4-ethylpiperazin-1-yl)-9-(3-(4-ethylpiperazin-1-yl)propyl)-9H-purin-2-amine (4)

A solution of compound 3 (1 g, 3.09 mmol) and triethylamine (1.29 mL, 9.28 mmol) in dry DMSO was taken in a seal tube. 1-ethylpiperazine (0.43 mL, 3.4 mmol) was added to the stirred mixture. The mixture was heated at 100° C. for 12 hours. Water was added to the reaction mixture.

The aqueous solution was extracted with chloroform. The organic layer was dried over Na$_2$SO$_4$ and evaporated under vacuum. The residue was purified by silica gel column chromatography, to provide compound 4 (0.65 g, 53%) as brown color gummy liquid. $^1$H NMR (600 MHz, CDCl$_3$) δ ppm 7.48 (s, 1H), 4.61 (s, 2H), 4.16-4.32 (m, 4H), 4.07 (t, J=6.75 Hz, 2H), 2.54 (t, J=5.03 Hz, 5H), 2.38-2.51 (m, 8H), 2.35 (t, J=1.00 Hz, 1H), 2.30 (t, J=6.90 Hz, 2H), 2.20 (m, 2H), 1.97 (q, J=6.84 Hz, 2H), 1.11 (t, J=7.19 Hz, 3H), 1.07 (t, J=7.23 Hz, 3H); ESI-MS m/z 402.47 (M+H).

Synthesis of 6-(4-ethylpiperazin-1-yl)-9-(−3-ethylpiperazin-1-yl)propyl)-N-(4-methoxybenzyl) 9H-purin-2-amine (5)

Compound 4 (0.3 g, 0.74 mmol) and 4-methoxybenzaldehyde (0.10 mL, 0.89 mmol) were dissolved in toluene (5 mL). One pinch of molecular sieves (3A powder) was added and the reaction stirred at 110° C. under N$_2$ atmosphere for 24 hours. Thereafter toluene was evaporated and sodium triacetoxyborohydride (0.3 g, 1.48 mmoL) was added. The reaction was stirred at room temperature for 1-2 hours. Reaction mixture was neutralized with NaHCO$_3$ solution. Organic part was extracted with CHCl$_3$ system. Column chromatography was done by using CHCl$_3$/CH$_3$OH system to get pure product of 5 (0.06 g, 45%) as a red liquid. $^1$HNMR (300 MHz, CDCl$_3$) δ ppm 7.27 (s, 3H), 6.50 (d, J=9 Hz, 2H), 4.97 (s, 1H), 4.54 (d, J=6 Hz, 2H), 4.24 (s, 3H), 4.07 (d, J=6 Hz, 2H), 3.79 (s, 3H), 2.54 (s, 5H), 2.42 (t, J=6 Hz, 5H), 2.30 (d, J=6 Hz, 3H), 1.98 (t, J=6 Hz, 2H), 1.13 (s, 1H), 1.07 (d, J=6 Hz, 6H); ESI-MS m/z 522.60 (M+H).

Synthesis of 6-(4-ethylpiperazin-1-yl)-9-(3-(4-ethylpiperazin-1-yl)propyl)-N-(4-fluorobenzyl)-9H-purin-2-amine (6)

Reaction of Compound 4 (0.3 g, 0.74 mmol) and 4-fluorobenzaldehyde (0.23 g, 0.88 mmol). Column chromatography was done by using CHCl$_3$/MeOH system to get pure product of 6 (0.05 g, yield 30%) as a gummy liquid. $^1$H NMR (300 MHz, CDCl$_3$) δ ppm 7.32 (s, 2H), 6.98 (m, 2H), 4.57 (d, J=6 Hz, 1H), 4.22 (s, 3H), 4.06 (d, J=6 Hz, 2H), 2.40-2.54 (m, 11H), 2.25 (d, J=9 Hz, 2H), 1.94-199 (m, 3H), 1.25 (s, 2H), 1.08 (t, J=9 Hz, 5H); ESI-MS m/z 510.45 (M+H).

Synthesis of N-(4-(diethylamino)benzyl)-6-(4-ethylpiperazin-1-yl)-9-(3-(4-ethylpiperazin-1-yl)propyl)-9H-purin-2-amine (7)

Reaction of compound 4 (0.18 g, 0.44 mmol) and 4-diethylamino benzaldehyde (0.137 mL, 1.34 mmol). The residue was purified by silica gel column chromatography, to produce compound 7 (0.11 g, 50%). $^1$H NMR (300 MHz, CDCL$_3$) ∥ ppm 1.10-1.16 (m, 12H) 1.99 (t, J=6.6 Hz, 2H) 2.32 (br. s., 2H), 2.40-2.49 (m, 10H), 2.54 (d, J=4.52 Hz, 4H), 3.33 (d, J=6.78 Hz, 4H) 4.09 (t, J=6.6 Hz, 2H), 4.24 (br. s., 4H), 4.48 (d, J=5.65 Hz, 2H), 4.91 (t, J=5.65 Hz, 1H) 6.63 (d, J=8.67 Hz, 2H), 7.22 (d, J=8.67 Hz, 2H), 7.46 (s, 1H); ESI-MS m/z 563.69 (M+H).

Synthesis of N-benzyl-6-(4-ethylpiperazin-1-yl)-9-(3-(4-ethylpiperazin-1-yl)propyl)-9H-purin-2-amine (8)

Reaction of compound 4 (0.18 g, 0.44 mmol) and benzaldehyde (0.137 mL, 1.34 mmol). The residue was purified by silica gel column chromatography, to produce compound 8 (0.11 g, 50%). $^1$H NMR (300 MHz, CDCl$_3$) δ ppm 7.50 (s, 1H), 7.27-7.44 (m, 5H), 5.07 (t, J=1.00 Hz, 1H), 4.66 (d, J=6.03 Hz, 2H), 4.19-4.38 (m, 4H), 4.12 (t, J=6.8 Hz, 2H), 2.55-2.60 (m, 6H), 2.41-2.52 (m, 10H), 2.32-2.37 (m, 2H), 2.02 (d, J=6.78 Hz, 2H), 1.14 (m, 6H); ESI-MS m/z 492.38 (M+H).

Example 2

Synthesis of 6-(4-ethylpiperazin-1-yl)-9(3-(4-ethylpiperazin-1-yl)propyl-2-(pyrrolidin-1-yl)-9H-purine (9)

Compound 4 (0.23 g, 0.57 mmol) was dissolved in DMF (5 mL), cooled to 0° C. and NaH (0.12 g, 0.85 mmol) and 1,4-dibromobutane (1.5 mL, 1.7 mmol) were added. The reaction was stirred under the N$_2$ atmosphere condition at 80° C. for 24 hours. Water was added to the reaction mixture and the organic layer was extracted with CHCl$_3$. Column chromatography was done by using CHCl$_3$ system to get the compound 9 (0.04 g, yield 30%) as a gummy liquid. $^1$H NMR (300 MHz, CDCl$_3$) δ ppm 7.41 (s, 1H), 4.24 (s, 5H), 4.07 (t, J=6 Hz, 3H), 3.5 (t, J=6 Hz, 5H), 2.42-2.46 (m, 11H), 2.30 (d, J=9 Hz, 5H), 1.89-1.94 (m, 7H), 1.06-1.13 (m, 8H). ESI-MS m/z 456.48 (M+H).

Example 3

Synthesis of N-(6-(4-ethylpiperazin-1-yl)-9-(3-(4-ethylpiperazin-1-yl)propyl)-9H-purin-2-yl)benzamide (10)

Benzoyl chloride (0.2 mL, 1.49 mmol) was added to a stirred solution of compound 4 (0.2 g, 0.498 mmol) and pyridine (0.24 mL, 2.99 mmol) in DCM. The mixture was stirred at room temperature for 10 hours. Solvent was removed under vacuum, the residue then washed with water. The aqueous solution was extracted with chloroform, washed with NaHCO$_3$, dried over Na$_2$SO$_4$ and evaporated under vacuum. The residue was purified by silica gel column chromatography to provide compound 10 (0.15 g, 60%). $^1$H NMR (300 MHz, CDCl$_3$) δ ppm 8.31 (s, 1H), 7.91 (d, J=7.1 Hz, 2H), 7.69 (s, 1H), 7.42-7.59 (m, 3H), 4.10-4.52 (m, 6H), 2.39-2.62 (m, 16H), 2.34 (t, J=6.68 Hz, 2H), 2.07 (t, J=1.00 Hz, 2H), 1.06-1.19 (m, 6H); ESI-MS m/z 506.52 (M+H).

Example 4

Synthesis of tert-butyl 2-((6-(4-ethylpiperazin-1-yl)-9-(3-(4-ethylpiperazin-1-yl)propyl)-9H-purin-2-yl) carbamoyl) pyrrolidine-1-carboxylate (11)

Oxalyl chloride (0.21 mL, 2.49 mmol) was added to DCM with catalytic amount of DMF at 0° C. Pyridine (0.24 mL, 2.99 mmol) was added to the reaction mixture and stirred for 15 mins. 1-(tert-butoxycarbonyl)pyrrolidine-2-carboxylic acid (0.32 g, 1.3 mmol) was introduced and stirred for 25 mins. Compound 4 (0.2 g, 0.49 mmol) was dissolved in dry DCM and introduced into the reaction mixture, stirred for 1 h. Water was added to the reaction mixture. The aqueous solution was extracted with CHCl$_3$. The organic layer was washed with NaHCO$_3$, dried over Na$_2$SO$_4$ and evaporated under vacuum. The residue was purified by silica gel column chromatography, to give compound 11 (0.15 g, 51%). $^1$H NMR (600 MHz, CDCl$_3$) δ ppm 7.65 (s, 1H), 4.23-4.71 (m, 4H), 4.15-4.20 (m, 2H), 3.45-3.64 (m, 2H), 2.42-2.67 (m, 14H), 2.31 (t, J=6.57 Hz, 3H), 2.15-2.27 (m, 2H), 1.96-2.08 (m, 5H), 1.91 (dd, J=10.45, 4.29 Hz, 2H), 1.43-1.53 (m, 9H), 1.07-1.15 (m, 6H); ESI-MS m/z: 599.66 (M+H).

Synthesis of N-(6-(4-ethylpiperazin-1-yl)-9-(3-(4-ethylpiperazin-1-yl)propyl)-9H-purin-2-yl) pyrrolidine-2-carboxamide (12)

Trifluoroacetic acid (0.1 mL, 1.3 mmol) was added to a solution of compound 11 (0.08 g, 0.13 mmol) in DCM at 0° C., stirred for 30 mins. The reaction was quenched using ammonia, DCM was removed under vacuum, the residue then dissolved in CHCl$_3$ (20 mL), and the organic layer was washed with water, dried and concentrated. The residue was purified by silica gel column chromatography, to produce compound 12 (0.06 g, 91%). $^1$H NMR (300 MHz, CDCl$_3$) δ ppm 9.85-10.14 (m, 1H), 7.69 (s, 1H), 4.27-4.49 (m, 4H), 4.23 (t, J=6.8 Hz, 2H), 3.91-4.00 (m, 1H) 3.06-3.15 (m, 2H), 2.58-2.64 (m, 5H), 2.48 (m, 10H), 2.35 (t, J=6.78 Hz, 2H), 2.19-2.30 (m, 2H), 2.16 (m, J=6.40 Hz, 2H), 2.09 (t, J=6.80 Hz, 2H), 1.75-1.88 (m, 2H), 1.14 (m, 6H); ESI-MS m/z 499.55 (M+H).

Example 5

Synthesis of N-(6-(4-ethylpiperazin-1-yl)-9-(3-(4-ethylpiperazin-1-yl) propyl)-9H-purin-2-yl)benzenesulfonamide (13)

Benzenesulfonyl chloride (0.2 g, 1.22 mmol) was added to a stirred solution of compound 4 (0.15 g, 0.37 mmol) and pyridine (0.18 mL, 2.24 mmol) in DCM. DMAP was added at catalytic amount. The mixture was stirred at room temperature for 10 h. Solvent was removed under vacuum, the residue then washed with water. The aqueous solution was extracted with chloroform, washed with NaHCO$_3$, dried over Na$_2$SO$_4$ and evaporated under vacuum. The residue was purified by silica gel column chromatography, to provide compound 13 (0.1 g, 50%). $^1$H NMR (300 MHz, CDCl$_3$) δ ppm 8.09 (d, J=7.16 Hz, 2H), 7.40-7.65 (m, 4H), 4.08 (m, J=6.60, 6.60 Hz, 6H), 3.02 (s, 1H), 2.36-2.64 (m, 16H), 2.29 (t, J=1.00 Hz, 2H), 1.94 (t, J=1.00 Hz, 2H), 1.02-1.16 (m, 6H); ESI-MS m/z 542.48 (M+H).

Example 6

Synthesis of N-(6-(4-ethylpiperazin-1-yl)-9-(3-(4-ethylpiperazin-1-yl)propyl)-9H-purin-2-yl)acetamide (14)

Acetyl chloride (0.1 mL, 1.49 mmol) was added to a stirred solution of compound 4 (0.2 g, 0.49 mmol) and pyridine (0.24 mL, 2.99 mmol) in DCM. The mixture was stirred at room temperature for 10 hours. Solvent was removed under vacuum, the residue then washed with water. The aqueous solution was extracted with chloroform. The organic layer was dried over Na$_2$SO$_4$ and evaporated under vacuum. The residue was purified by silica gel column chromatography, to give compound 14 (0.11 g, 82%). $^1$H NMR (300 MHz, DMSO) δ ppm 7.75 (s, 1H), 7.64 (s, 1H), 4.10-4.48 (m, 6H), 2.53-2.57 (m, 6H), 2.36-2.50 (m, 10H), 2.29 (t, J=6.78 Hz, 3H), 1.93-2.05 (m, 4H), 1.06-1.16 (m, 6H); ESI-MS m/z 444.43 (M+H).

Example 7

Synthesis of iso-butyl (1-(6-(4-ethylpiperazin-1-yl)-9-(3-(4-ethylpiperazin-1-yl)propyl)-9H-purin-2-yl) amino)-1-oxo-3-phenylpropan-2-yl)carbamate (15)

A solution of compound 4 (0.25 g, 0.62 mmol) and 2-((tert-butoxycarbonyl)amino)-3-phenylpropanoic acid (0.16 g, 0.62 mmol) in pyridine was added POCl$_3$ (0.06 mL, 0.68 mmol) at −10° C. and stirred for 2 hours. The reaction mixture was quenched with ammonia until it becomes neutral pH. Ice was added to the mixture. The aqueous layer was extracted with chloroform, dried over Na$_2$SO$_4$ and evaporated under vacuum. The residue was purified by silica gel column chromatography to provide compound 15 (0.21 g, 53%). $^1$H NMR (300 MHz, CDCl$_3$) δ ppm 7.89-7.98 (m, 1H), 7.65 (s, 1H), 7.19-7.28 (m, 5H), 5.15-5.29 (m, 1H), 4.08-4.44 (m, 6H), 3.25 (dd, J=1.00 Hz, 1H), 3.04-3.16 (m, 1H), 2.37-2.60 (m, 15H), 2.29 (t, J=1.00 Hz, 2H), 1.93-2.08 (m, 4H), 1.33-1.47 (m, 9H), 1.11 (m, 6H); ESI-MS m/z 649.83 (M+H).

Synthesis of 4-((dimethylamino)methyl)-N-(6-(4-ethylpiperazin-1-yl)-9-(3-(4-ethylpiperazin-1-yl) propyl)-9H-purin-2-yl)benzamide (16)

Reaction of Compound 4 (0.2 g, 0.5 mmol) and 4-((dimethylamino)methyl)benzoic acid (0.13 g, 0.6 mmol) was done according to procedure B. Then column chromatography was done by using CHCl$_3$/MeOH system to get the pure product 16 (yield 53%). $^1$H NMR (300 MHz, DMSO-d$_6$) δ ppm 8.06 (s, —NH), 7.86 (d, J=8.4 Hz, 2H), 7.70 (s, 1H), 7.40 (d, J=7.8 Hz, 2H), 4.12 (m, 6H), 3.97 (t, J=6.0 Hz, 2H), 3.16-3.09 (m, 2H), 2.72 (s, 6H), 2.47-2.41 (m, 8H), 2.40-2.37 (m, 4H), 2.27-2.25 (m, 4H), 1.96-1.84 (m, 2H), 1.03 (t, J=6.3 Hz, 6H). ESI-MS m/z 563.32 (M+H).

Example 8

Synthesis of 6-chloro-9-(3-(4-ethylpiperazin-1-yl) propyl)-9H-purin-2-amine (17)

Compound 1 (2 g, 0.01 mmol) was dissolved in DMF (5 mL), and stirred for 2-3 hours under the N2 atmosphere condition at the 120° C. get the clear solution. Potassium carbonate and (1.6 g, 0.1 mmol), (3-chloropropyl)-4-ethylpiperazine) were added to the reaction mixture and stirred for 12 hours. Water was added to the reaction and organic layer was separated with CHCl$_3$. Column chromatography was done by using CHCl$_3$/CH$_3$OH system, to get the compound 17 (1.2 gm, 50% yield) as a thick gummy liquid. $^1$H NMR (300 MHz, CDCl$_3$) δ ppm 7.81 (s, 1H), 5.21 (s, 2H), 4.14-4.19 (t, 2H), 2.43 (t, 10H), 2.29 (d, J=6 Hz, 3H), 2.2 (t, J=6 Hz, 3H), 1.08 (t, 4H); ESI-MS m/z 324.26 (M+H).

Synthesis of (4-(2-amino-9-(3-(4-ethylpiperazin-1-yl)propyl)-9H-purin-6-yl)piperazin-1-yl)(phenyl) methanone (18)

Compound 17 was dissolved in acetonitrile (5 mL), potassium carbonate (1.2 g, 0.03 mmol) and phenyl(piperazine-1-yl) methanone (0.84 g, 0.03 mmol) were added. The reaction was stirred for 2 hours under N$_2$ atmosphere condition at 100° C. Acetonitrile was evaporated under the vacuum, then water was added to the reaction mixture to get precipitate which was filter off to get precipitate (0.8 g, yield 70%) of product 18. $^1$H NMR (300 MHz, CDCl$_3$) δ ppm 7.49 (s, 1H), 7.42 (d, J=9 Hz, 4H), 4.63 (s, 2H), 4.26 (s, 3H), 4.09 (t, J=6 Hz, 2H), 3.89 (s, 2H), 3.54 (s, 2H), 2.42 (d, J=6 Hz, 8H), 2.28-2.40 (m, 3H), 1.85-2.03 (m, 3H), 1.08 (t, J=6 Hz, 3H). ESI-MS m/z 478.34 (M+H).

Synthesis of 4-(2-(4-(diethylamino)benzyl)amino-9-(3-(4-ethylpiperazin-1-yl)propyl)-9H-purine-6-yl) piperazin-1-yl)(phenyl)methanone (19)

Compound 18 (0.2 g, 0.41 mmol) and 4-diethyl amino-benzaldehyde (0.07 g, 0.41 mmol) was dissolved in toluene (5 mL). Molecular sieves (3 Å powder) was added and the reaction stirred at 110° C. under N$_2$ atmosphere for 12-16 hours. Thereafter toluene was evaporated and sodium triacetoxyborohydride (0.18 g, 0.82 mmol) to the reaction mixture and the mixture was dissolved in DCE (5 mL). Reaction mixture was kept in room temperature and allowed to stir for 2-3 hours. After completion of the reaction, it was neutralized with NaHCO$_3$ solution. Organic part was extracted with 20% CH$_3$OH/CHCl$_3$ system. Column Chromatography was done by using CHCl$_3$ system to get pure product of 19, (0.06 g, yield 52%) as a gummy liquid. $^1$H NMR (300 MHz, CDCl$_3$) δ ppm 7.47 (s, 6H), 7.19 (s, 2H), 6.63 (d, J=9 Hz, 2H), 4.96 (s, 1H), 4.45 (d, J=9 Hz, 2H), 4.21-4.27 (m, 3H), 4.07-4.12 (m, 2H), 3.87 (s, 2H), 3.29-3.36 (m, 4H), 2.44-2.49 (m, 9H), 2.32 (d, J=6 Hz, 4H), 1.98 (d, J=6 Hz, 3H), 1.25 (s, 2H), 1.10-1.16 (m, 9H). ESI-MS m/z 639.74 (M+H).

Synthesis of (4-(9-(3-(4-ethylpiperazin-1-yl)propyl)-2-(pyrrolidin-1-yl)-9H-purin-6-yl)piperazin-1-yl)(phenyl)methanone (20)

Compound 18 (0.25 g, 0.52 mmol) was dissolved in dry DMF (5 mL), the reaction mixture was cooled to −10° C. and NaH (0.02 g 1.4 mmol) was added. The reaction mixture was allowed to stir for one hour at cold condition. Then 1,4-dibromo butane (0.06 g, 0.52 mmol) was added to it and allowed to stir for further 12 hours under the N$_2$ atmosphere at 60° C. After completion of the reaction, organic layer was extracted by using the CHCl$_3$/CH$_3$OH system. Column chromatography was done by using CHCl$_3$/ system to get pure product 20 (0.02 g, yield 30%) as a red colour gummy liquid. $^1$H NMR (300 MHz, CDCl$_3$) δ ppm 7.46 (s, 1H), 6.98 (t, J=9 Hz, 3H), 4.57 (d, J=6 Hz, 1H), 4.22 (s, 2H), 4.07 (s, 2H), 2.40-2.54 (m, 11H), 2.28 (d, J=6 Hz, 2H), 1.97 (d, J=9 Hz, 3H), 1.25 (s, 2H), 1.08 (t, J=9 Hz, 5H). ESI-MS m/z 532.57 (M+H).

Synthesis of (4-(9-(3-(4-ethylpiperazin-1-yl)propyl)-2-((4-methoxybenzyl)amino)-9H-purin-6-yl)piper-azin-1-yl)(phenyl)methanone (21)

Reaction of compound 18 (0.200 g, 0.42 mmol) and 4-methoxybenzaldehyde (0.137 mL, 1.34 mmol) was done as discussed above for compound 5. The residue was purified by silica gel column chromatography, to produce compound 21 (0.100 g, 66%). $^1$H NMR (300 MHz, CDCl$_3$) δ ppm 7.44 (s, 1H), 7.42 (m, 5H), 7.27 (d, J=9.0 Hz, 2H), 6.83 (d, J=9.0 Hz, 2H), 5.25 (t, J=1.00 Hz, 1H), 4.52 (d, J=6.03 Hz, 2H), 4.20 (m, 4H), 4.07 (t, J=6.78 Hz, 2H), 3.85 (m, 2H), 3.78 (s, 3H), 3.51 (m, 2H), 2.50-2.57 (m, 10H), 2.34 (t, J=6.78 Hz, 2H), 1.96-1.98 (m, 2H), 1.12 (t, J=6.01, 3H); ESI-MS m/z 598.14 (M+H$^+$).

Synthesis of (4-(9-(3-(4-ethylpiperazin-1-yl)propyl)-2-((4-fluorobenzyl)amino)-9H-purin-6-yl)piperazin-1-yl)(phenyl)methanone (22)

Reaction of compound 18 (0.200 g, 0.42 mmol) and 4-flurobenzaldehyde (0.06 mL, 1.34 mmol) was done as discussed above for compound 5. The residue was purified by silica gel column chromatography, to produce compound 22 (yield 63%). $^1$H NMR (300 MHz, CDCl$_3$) δ ppm 7.43 (m, 6H), 7.31 (d, J=9.0 Hz, 2H), 6.99 (t, J=6.0 Hz, 2H), 5.29 (t, J=1.00 Hz, 1H), 4.55 (d, J=6.03 Hz, 2H), 4.22 (m, 4H), 4.07 (t, J=6.78 Hz, 2H), 3.85 (m, 2H), 3.51 (m, 2H), 2.79-2.69 (m, 10H), 2.40 (t, J=6.78 Hz, 2H), 1.99 (t, J=6.0 Hz, 2H), 1.28 (t, J=6.01, 3H); ESI-MS m/z 586.05 (M+H).

Synthesis of 6-(4-cyclopentylpiperazin-1-yl)-9-(3-(4-ethyl piperazin-1-yl)propyl)-9H-purin-2-amine (23)

Compound 17 (0.1 g, 0.36 mmol) was dissolved in acetonitrile (5 mL) and potassium carbonate (0.04 g, 0.36 mmol) and 1-cyclopentylpiperazine (0.05 g, 0.37 mmol) were added. The reaction was stirred under the N$_2$ atmospheric condition at 100° C. for 12 hours. Organic layer was extracted with CHCl$_3$ system and column chromatography was done by using CH$_3$OH and CHCl$_3$ system to separate compound 23 (0.02 g, yield 40%) as a brown liquid. $^1$H NMR (300 MHz, CDCl$_3$) δ ppm 7.46 (s, 1H), 4.71 (s, 2H), 4-4.10 (m, 5H), 2.24-2.56 (m, 18H), 1.93 (t, J=6 Hz, 6H), 1-1.05 (t, J=6 Hz, 5H). ESI-MS m/z 442.45 (M+H).

Example 9

Synthesis of 6-(4-cyclopentylpiperazin-1-yl)-N-(4-diethylamino)benzyl)-9-(3-(4-ethylpiperazine-1-yl) propyl)-9H-purine-2-amine (24)

Compound 23 (0.25 g, 0.34 mmol) and 4-diethyl amino-benzaldehyde (0.20 g, 0.60 mmol) was dissolved in toluene (5 mL). Molecular sieves (3 Å powder) was added and the reaction stirred at 110° C. under N$_2$ atmosphere for 12-16 hours. Thereafter toluene was evaporated and sodium triacetoxyborohydride (0.2 g, 0.68 mmol) was added to the reaction mixture and stirred for 2-3 hours at room temperature. Reaction mixture was neutralized with NaHCO$_3$ solution. Organic part was extracted with CHCl$_3$. Column chromatography was done by using CHCl$_3$:CH$_3$OH system to get pure product of 24 (yield 55%) as a gummy liquid. $^1$H NMR (300 MHz, CDCl$_3$) δ ppm 7.43 (s, 1H), 7.19 (d, J=9.0 Hz, 2H), 6.61 (d, J=9 Hz, 2H), 4.45 (d, J=3 Hz, 2H), 4.42 (s, 3H) 4.06 (t, J=6. Hz, 2H), 3.27-3.34 (m, 3H), 2.50-2.57 (m, 5H), 2.37-2.42 (m, 9H), 2.28 (d, J=6 Hz, 3H), 1.97 (t, J=6. Hz, 2H), 1.86 (s, 2H), 1.68 (d, J=6. Hz, 2H), 1.41-1.55 (m, 4H), 1.03 (m, 10H). ESI-MS m/z 603.64 (M+H).

Synthesis of 6-(4-cyclopentylpiperazin-1-yl)-9-(3-(4-ethylpiperazin-1-yl)propyl)-N-(4-fluorobenzyl)-9H-purin-2-amine (25)

Reaction of compound 23 (0.20 g, 0.42 mmol) and 4-flurobenzaldehyde (0.06 mL, 1.34 mmol) was done as discussed above for compound 5. The residue was purified by silica gel column chromatography, to produce compound 25 (yield 61%). $^1$H NMR (300 MHz, CDCl$_3$) δ ppm 7.46 (s, 1H), 7.32 (dd, J=9.0 Hz, 2H), 6.98 (t, J=9.0 Hz, 2H), 5.02 (m, 1H), 4.57 (d, J=6.03 Hz, 2H), 4.22 (m, 4H), 4.07 (t, J=6.78 Hz, 2H), 2.59-2.56 (m, 4H), 2.52-2.37 (m, 10H), 2.30

(t, J=6.78 Hz, 2H), 1.96 (m, 2H), 1.70 (m, 2H), 1.40-1.43 (m, 4H), 1.08 (t, J=6.01, 3H); ESI-MS m/z 450.28 (M+H).

Synthesis of 6-(4-cyclopentylpiperazin-1-yl)-9-(3-(4-ethylpiperazin-1-yl)propyl)-N-(4-methoxybenzyl)-9H-purin-2-amine (26)

Reaction of Compound 23 (0.2 g, 0.45 mmol) and 4-methoxybenzaldehyde (0.066 mL, 0.54 mmol was done as discussed above for compound 5. Then column chromatography was done by using $CHCl_3$/MeOH system to get the pure product 26 (yield 56%) as a gummy solid. $^1$H NMR (300 MHz, $CDCl_3$) δ ppm 7.45 (s, 1H), 7.29 (d, J=8.7 Hz, 2H), 6.85 (d, J=8.7 Hz, 2H), 5.0 (t, J=5.7 Hz, 1H), 4.54 (d, J=6.0 Hz, 2H), 4.29 (m, 4H), 4.08 (t, J=6.6 Hz, 2H), 3.79 (s, 3H), 2.65 (m, 4H), 2.57-2.53 (m, 8H), 2.35 (t, J=6.6 Hz, 2H), 2.03-1.97 (m, 3H), 1.91 (m, 2H), 1.73 (m, 2H), 1.55 (m, 2H), 1.26 (m, 4H), 1.15 (t, J=7.2 Hz, 3H). ESI-MS m/z 562.34 (M+H).

Synthesis of N-(6-(4-cyclopentylpiperazin-1-yl)-9-(3-(4-ethylpiperazin-1-yl)propyl)-9H-purin-2-yl)-4-((dimethylamino)methyl)benzamide (27)

A solution of compound 23 (0.10 g, 0.23 mmol) and 4-((dimethylamino)methyl)benzoic acid (0.048 g, 0.27 mmol) in pyridine was added $POCl_3$ (0.03 mL, 0.35 mmol) at 0° C. and stirred for 2 hours. The reaction mixture was poured into crushed ice and neutralised with saturated $Na_2CO_3$ solution. The aqueous layer was extracted with chloroform, dried over $Na_2SO_4$ and evaporated under vacuum. The residue was purified by silica gel column chromatography to give compound 27 (yield 53%). $^1$H NMR (300 MHz, $CDCl_3$) δ ppm 8.30 (s, —NH), 7.87 (d, J=7.8 Hz, 2H), 7.67 (s, 1H), 7.43 (d, J=7.5 Hz, 2H), 4.22 (t, J=6.9 Hz, 1H), 3.50 (s, 2H), 2.64 (m, 8H), 2.55 (m, 8H), 2.37 (t, J=6.6 Hz, 2H), 2.27 (s, 6H), 2.06 (t, J=6.6 Hz, 2H), 1.9 (m, 2H), 1.72 (m, 2H), 1.59-1.44 (m, 4H), 1.25 (m, 4H), 1.15 (t, J=7.5 Hz, 3H). ESI-MS m/z 603.26 (M+H).

Example 10

Synthesis of 6-(4-cyclopentylpiperazin-1-yl)-9H-purin-2-amine (28)

Compound 1 (0.5 g, 2.95 mmol) was dissolved in acetonitrile (8 mL) and potassium carbonate (1.63 g, 11.8 mmol) and 1-cyclopentylpiperazine (0.91 g, 5.9 mmol) were added. The reaction was stirred under the $N_2$ atmospheric condition at 100° C. for 12 hours. Organic layer was extracted with $CHCl_3$ system and column chromatography was done by using $CH_3OH$ and $CHCl_3$ system to give compound 28 (yield 60%) as a off-white solid. $^1$H NMR (300 MHz, DMSO-$d_6$) δ ppm 7.66 (s, 1H), 5.72 (s, —$NH_2$), 4.09 (m, 4H), 2.46 (t, J=4.2 Hz, 4H), 2.42-2.39 (m, 1H), 1.61-1.50 (m, 4H), 1.43-1.29 (m, 4H). ESI-MS m/z 288.14 (M+H).

Synthesis of 6-(4-cyclopentylpiperazin-1-yl)-9-(3-(pyrrolidin-1-yl)propyl)-9H-purin-2-amine (29)

1-(3-chloropropyl)pyrrolidine (0.77 g, 5.22 mmol) was added to a stirred suspension of compound 28 (1 g, 3.48 mmol) and potassium carbonate (0.96 g, 6.96 mmol) in dry DMF and the reaction mixture was heated for 12 hours at 80° C. Water was added to the reaction mixture. The aqueous solution was extracted with chloroform and the organic layer was dried over $Na_2SO_4$ and evaporated under vacuum. The residue was purified by silica gel column chromatography eluting with 5% methanol in chloroform, to give compound 29 (yield 65%) as colorless liquid. $^1$H NMR (300 MHz, $CDCl_3$) δ ppm 7.49 (s, 1H), 4.63 (s, —$NH_2$), 4.24 (m, 4H), 4.09 (t, J=6.9 Hz, 2H), 2.59 (t, J=5.1 Hz, 4H), 2.50 (m, 4H), 2.46-2.41 (m, 4H), 2.16 (s, 1H), 2.01 (m, 2H), 1.87-1.83 (m, 2H), 1.72-1.63 (m, 4H), 1.52-1.41 (m, 4H). ESI-MS m/z 399.12 (M+H).

Synthesis of 6-(4-cyclopentylpiperazin-1-yl)-N-(4-methoxybenzyl)-9-(3-(pyrrolidin-1-yl)propyl)-9H-purin-2-amine (30)

Reaction of Compound 29 (0.2 g, 0.50 mmol) and 4-methoxybenzaldehyde (0.07 mL, 0.60 mmol) was done as discussed above for compound 5. Then column chromatography was done by using $CHCl_3$/MeOH system to get the pure product 30 (yield 59%). $^1$H NMR (300 MHz, $CDCl_3$) δ ppm 7.47 (s, 1H), 7.29 (d, J=8.4 Hz, 2H), 6.84 (d, J=8.4 Hz, 2H), 4.99 (t, J=5.7 Hz, —NH), 4.54 (d, J=5.7 Hz, 2H), 4.24 (m, 4H), 4.11 (t, J=7.2 Hz, 2H), 3.79 (s, 3H), 2.61-2.58 (m, 8H), 2.50 (t, J=7.2 Hz, 4H), 2.12-2.04 (m, 2H), 1.88 (m, 3H), 1.81 (m, 4H), 1.71 (m, 2H), 1.61-1.53 (m, 2H). ESI-MS m/z 519.19 (M+H).

Synthesis of N-(6-(4-cyclopentylpiperazin-1-yl)-9-(3-(pyrrolidin-1-yl)propyl)-9H-purin-2-yl)-4-((dimethylamino)methyl)benzamide (31)

Reaction of Compound 29 (0.1 g, 0.25 mmol) and 4-((dimethylamino)methyl)benzoic acid (0.065 g, 0.30 mmol) was done as discussed above for compound 27. Then column chromatography was done by using $CHCl_3$/MeOH system to get the pure product 31 (yield 53%). $^1$H NMR (300 MHz, $CDCl_3$) δ ppm 8.33 (s, —NH), 7.87 (d, J=7.8 Hz, 2H), 7.67 (s, 1H), 7.42 (d, J=8.1 Hz, 2H), 4.23 (t, J=6.6 Hz, 2H), 3.48 (s, 2H), 2.62-2.48 (m, 12H), 2.25 (s, 6H), 2.12 (t, J=6.6 Hz, 1H), 1.61-1.52 (m, 2H), 1.47-1.41 (m, 2H), 1.33-1.28 (m, 4H), 0.87-0.82 (m, 8H). ESI-MS m/z 560.34 (M+H).

Synthesis of 6-(4-cyclopentylpiperazin-1-yl)-N-(4-fluorobenzyl)-9-(3-(pyrrolidin-1-yl)propyl)-9H-purin-2-amine (32)

Reaction of Compound 29 (0.1 g, 0.25 mmol) and 4-fluorobenzaldehyde (0.03 mL, 0.3 mmol) was done as discussed above for compound 5. Then column chromatography was done by using $CHCl_3$/MeOH system to get the pure product 32 (yield 52%). 1H NMR (300 MHz, $CDCl_3$) δ ppm 7.47 (s, 1H), 7.35-7.31 (m, 2H), 6.98 (t, J=8.7 Hz, 2H), 5.07 (t, J=6.0 Hz, —NH), 4.57 (d, J=6.0 Hz, 2H), 4.23 (m, 4H), 4.09 (t, J=6.9 Hz, 2H), 2.59-2.45 (m, 12H), 2.04 (m, 1H), 1.73-1.68 (m, 2H), 1.59-1.54 (m, 2H), 1.25 (m, 4H), 0.87-0.85 (m, 4H). ESI-MS m/z 507.18 (M+H).

Example 11

Synthesis of 6-(4-ethylpiperazin-1-yl)-9-(3-(pyrrolidin-1-yl)propyl)-9H-purin-2-amine (33)

A solution of compound 3 (1 g, 3.09 mmol) and triethylamine (1.29 mL, 9.28 mmol) in dry DMSO was taken in a seal tube. Pyrrolidine (0.28 mL, 3.4 mmol) was added to the stirred mixture. The mixture was heated at 100° C. for 12 hours. Water was added to the reaction mixture. The aqueous solution was extracted with chloroform. The organic layer was dried over $Na_2SO_4$ and evaporated under vacuum. The residue was purified by silica gel column chromatography, to provide compound 33 (72%). $^1$H NMR (300 MHz, $CDCl_3$) δ ppm 7.50 (s, 1H), 4.61 (s, —$NH_2$), 4.25 (m, 4H), 4.11 (t, J=6.9 Hz, 2H), 2.56-2.53 (m, 8H), 2.49-2.42 (m, 6H), 2.20 (m, 2H), 2.04 (q, J=6.9 Hz, 2H), 1.12 (t, J=7.2 Hz, 3H). ESI-MS m/z 359.11 (M+H).

Synthesis of 6-(4-ethylpiperazin-1-yl)-N-(4-methoxybenzyl)-9-(3-(pyrrolidin-1-yl)propyl)-9H-purin-2-amine (34)

Reaction of Compound 33 (0.08 g, 0.22 mmol) and 4-methoxybenzaldehyde (0.03 mL, 0.27 mmol) was done as discussed above for compound 5. Then column chromatography was done by using $CHCl_3$/MeOH system to get the pure product 34 (58%). $^1$H NMR (300 MHz, $CDCl_3$) δ ppm 7.47 (s, 1H), 7.29 (d, J=8.4 Hz, 2H), 6.84 (d, J=8.4 Hz, 2H), 4.98 (t, J=5.4 Hz, —NH), 4.54 (d, J=6.0 Hz, 2H), 4.23 (m, 4H), 4.10 (t, J=6.9 Hz, 2H), 3.79 (s, 3H), 2.53-2.44 (m, 12H), 2.05-1.99 (m, 6H), 1.12 (t, J=7.2 Hz, 3H). ESI-MS m/z 479.21 (M+H).

Synthesis of 4-((dimethylamino)methyl)-N-(6-(4-ethylpiperazin-1-yl)-9-(3-(pyrrolidin-1-yl)propyl)-9H-purin-2-yl)benzamide (35)

Reaction of Compound 33 (0.09 g, 0.25 mmol) and 4-((dimethylamino)methyl)benzoic acid (0.065 g, 0.30 mmol)) was done as discussed above for compound 27. Then column chromatography was done by using $CHCl_3$/MeOH system to get the pure product 35 (56%). $^1$H NMR (300 MHz, $CDCl_3$) δ ppm 8.33 (s, —NH), 7.87 (d, J=8.1 Hz, 2H), 7.69 (s, 1H), 7.43 (d, J=8.1 Hz, 2H), 4.24 (t, J=6.9 Hz, 2H), 3.49 (s, 2H), 2.67 (m, 4H), 2.58 (t, J=4.8 Hz, 4H), 2.47 (q, J=7.2 Hz, 2H), 2.26 (s, 6H), 2.15 (t, J=6.9 Hz, 2H), 2.01 (m, 4H), 1.85 (m, 2H), 1.25 (m, 4H), 1.13 (t, J=6.9 Hz, 3H). ESI-MS m/z 520.09 (M+H).

Synthesis of 6-(4-ethylpiperazin-1-yl)-N-(4-fluorobenzyl)-9-(3-(pyrrolidin-1-yl)propyl)-9H-purin-2-amine (36)

Reaction of Compound 33 (0.08 g, 0.22 mmol) and 4-fluorobenzaldehyde (0.03 mL, 0.3 mmol) was done as discussed above for compound 5. Then column chromatography was done by using $CHCl_3$/MeOH system to get the pure product 36 (58%). $^1$H NMR (300 MHz, $CDCl_3$) δ ppm 7.74 (s, 1H), 7.35-7.31 (m, 2H), 7.01 (t, J=8.7 Hz, 2H), 4.59 (br. s, 2H), 4.36 (t, J=5.7 Hz, 2H), 2.54 (m, 8H), 2.48-2.41 (m, 4H), 2.28-2.20 (m, 2H), 1.77 (m, 2H), 1.63 (m, 4H), 1.25 (m, 2H), 1.11 (t, J=6.9 Hz, 3H). ESI-MS m/z 467.15 (M+H).

Example 12

Synthesis of (4-(2-amino-9-(3-(4-ethylpiperazin-1-yl)propyl)-9H-purin-6-yl)piperazin-1-yl)(cyclopentyl)methanone (37)

Compound 17 was dissolved in acetonitrile (5 mL), potassium carbonate (1.2 g, 0.03 mmol) and cyclopentyl (piperazine-1-yl)methanone (0.84 g, 0.03 mmol) were added. The reaction was stirred for 2 hours under $N_2$ atmosphere condition at 100° C. acetonitrile was evaporated under the vacuum, then water was added to the reaction mixture to get precipitate which was filter off to get precipitate (yield 75%) of product 37. $^1$H NMR (300 MHz, $CDCl_3$) δ ppm 7.48 (s, 1H), 5.09 (t, J=1.00 Hz, 1H), 4.57 (d, J=6.03 Hz, 2H), 4.18-4.25 (m, 4H), 4.11 (t, J=7.5 Hz, 2H), 3.74 (m, 2H), 3.64 (m, 2H), 2.91 (m, 1H), 2.79-2.69 (m, 10H), 2.34 (t, J=6.78 Hz, 2H), 2.00 (m, 4H), 1.98 (m, 2H), 1.75 (m, 4H), 1.59 (m, 2H), 1.16 (t, J=6.01, 3H); ESI-MS m/z 590.30 (M+H).

Synthesis of cyclopentyl(4-(2-((4-(diethylamino)benzyl)amino)-9-(3-(4-ethylpiperazin-1-yl)propyl)-9H-purin-6-yl)piperazin-1-yl)methanone (38)

Reaction of compound 37 (0.20 g, 0.41 mmol) and 4-(diethylamino)benzaldehyde (0.88 gm, 1.34 mmol) was done as discussed above for compound 5. The residue was purified by silica gel column chromatography, to produce compound 38 (68%). $^1$H NMR (300 MHz, $CDCl_3$) δ ppm 7.45 (s, 1H), 7.20 (d, J=9.0 Hz, 2H), 6.63 (d, J=9.0 Hz, 2H), 5.09 (s, 1H), 4.47 (d, J=6.03 Hz, 2H), 4.17 (m, 4H), 4.10 (t, J=6.78 Hz, 2H), 3.73 (m, 2H), 3.62 (m, 2H), 3.34 (m, 4H), 2.91 (m, 1H), 2.60 (m, 8H), 2.33 (m, 2H), 2.01 (m, 6H), 1.84 (m, 4H), 1.14 (t, J=6.01, 9H); ESI-MS m/z 631.16 (M+H).

Synthesis of cyclopentyl(4-(9-(3-(4-ethylpiperazin-1-yl)propyl)-2-((4-methoxybenzyl)amino)-9H-purin-6-yl)piperazin-1-yl)methanone (39)

Reaction of compound 37 (0.200 g, 0.41 mmol) and 4-methoxybenzaldehyde (0.05 mL, 1.34 mmol) was done as discussed above for compound 5. The residue was purified by silica gel column chromatography, to produce compound 39 (63%). $^1$H NMR (300 MHz, $CDCl_3$) δ ppm 7.48 (s, 1H), 7.31 (d, J=9.0 Hz, 2H), 6.86 (d, J=9.0 Hz, 2H), 5.09 (t, J=1.00 Hz, 1H), 4.57 (d, J=6.03 Hz, 2H), 4.18-4.25 (m, 4H), 4.11 (t, J=7.5 Hz, 2H), 3.81 (s, 3H), 3.74 (m, 2H), 3.64 (m, 2H), 2.91 (m, 1H), 2.79-2.69 (m, 10H), 2.34 (t, J=6.78 Hz, 2H), 2.00 (m, 4H), 1.98 (m, 2H), 1.75 (m, 4H), 1.59 (m, 2H), 1.16 (t, J=6.01, 3H); ESI-MS m/z 590.30 (M+H).

Synthesis of cyclopentyl(4-(9-(3-(4-ethylpiperazin-1-yl)propyl)-2-((4-fluorobenzyl)amino)-9H-purin-6-yl)piperazin-1-yl)methanone (40)

Reaction of compound 37 (0.200 g, 0.41 mmol) and 4-flurobenzaldehyde (0.05 mL, 1.34 mmol) was done as discussed above for compound 5. The residue was purified by silica gel column chromatography, to produce compound 40 (61%). $^1$H NMR (300 MHz, $CDCl_3$) δ ppm 7.47 (s, 1H), 7.32 (d, J=9.0 Hz, 2H), 6.99 (t, J=6.0 Hz, 2H), 5.09 (t, J=1.00 Hz, 1H), 4.57 (d, J=6.03 Hz, 2H), 4.22-4.15 (m, 4H), 4.08 (t, J=6.78 Hz, 2H), 3.71 (m, 2H), 3.60 (m, 2H), 2.91 (m, 1H), 2.79-2.69 (m, 10H), 2.34 (t, J=6.78 Hz, 2H), 2.00 (m, 4H), 1.98 (m, 2H), 1.75 (m, 4H), 1.59 (m, 2H), 1.16 (t, J=6.01, 3H); ESI-MS m/z 578.37 (M+H).

TABLE 1
Compound with general formula (I) composition of the Invention
| Comp | R1 | R₂ | R₃ |
|---|---|---|---|
| 4 | Et |  | 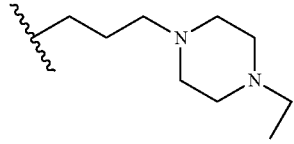 [SMILES: *CCCN1CCN(CC)CC1] |
| 5 | Et | 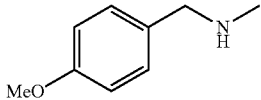 | 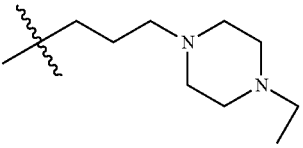 [SMILES: *CCCN1CCN(CC)CC1] |
| 6 | Et | 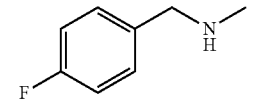 | 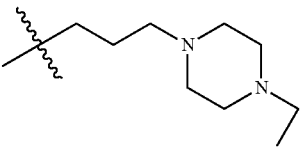 [SMILES: *CCCN1CCN(CC)CC1] |
| 7 | Et | 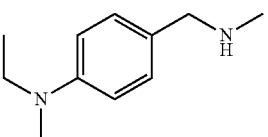 | 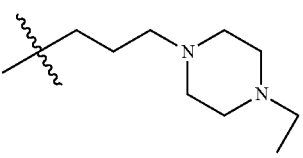 [SMILES: *CCCN1CCN(CC)CC1] |
| 8 | Et | 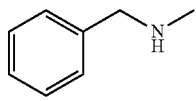 | 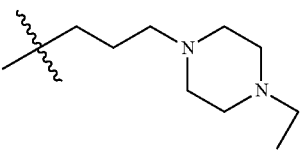 [SMILES: *CCCN1CCN(CC)CC1] |
| 9 | Et | 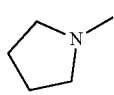 | 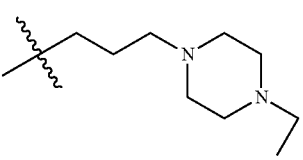 |
| 10 | Et | 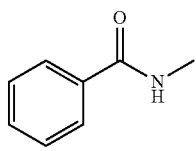 | 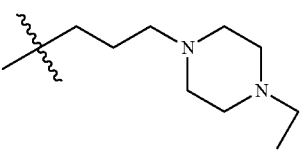 [SMILES: *CCCN1CCN(CC)CC1] |
| 11 | Et | 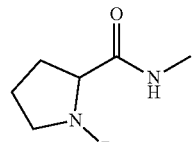 | 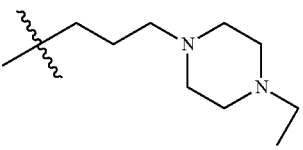 [SMILES: *CCCN1CCN(CC)CC1] |
| 12 | Et | 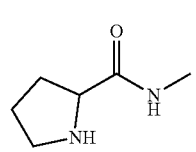 | 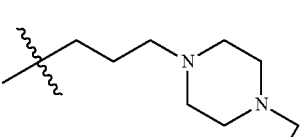 |

TABLE 1-continued
Compound with general formula (I) composition of the Invention
| Comp | R1 | R₂ | R₃ |
|------|----|----|----|
| 13 | Et | 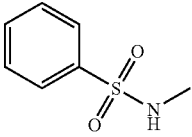 | 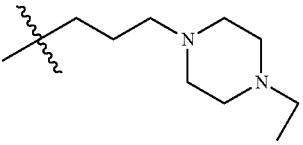 |
| 14 | Et | 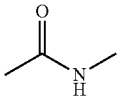 | 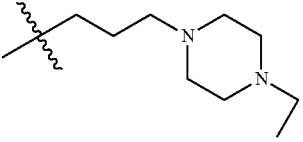 [SMILES: *CCCN1CCN(CC)CC1] |
| 15 | Et | 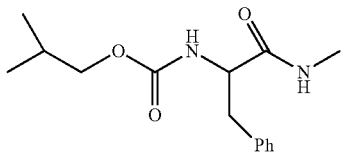 | 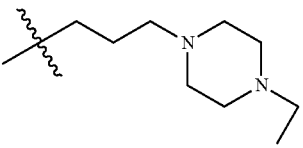 [SMILES: *CCCN1CCN(CC)CC1] |
| 16 | Et | 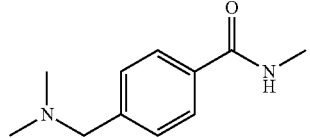 | 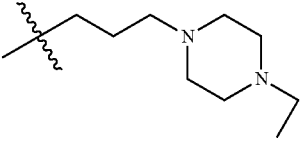 [SMILES: *CCCN1CCN(CC)CC1] |
| 18 | 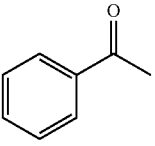 | H₂N— |  |
| 19 | 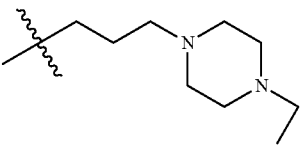 [SMILES: *CCCN1CCN(CC)CC1] | 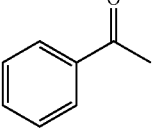 | 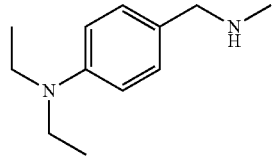 |
| 20 | 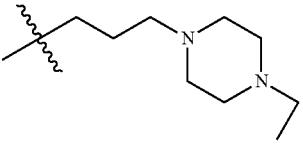 [SMILES: *CCCN1CCN(CC)CC1] | 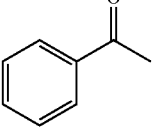 | 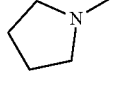 |
| 21 | 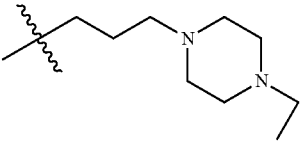 [SMILES: *CCCN1CCN(CC)CC1] | 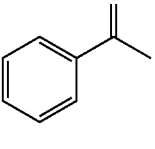 | 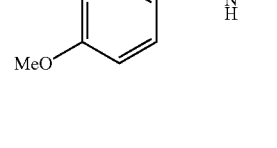 |
| 22 | 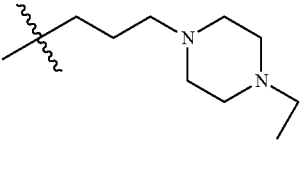 [SMILES: *CCCN1CCN(CC)CC1] | 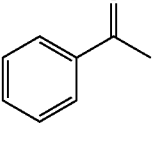 | 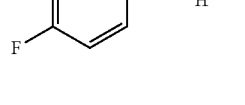 |

TABLE 1-continued

Compound with general formula (I) composition of the Invention

| Comp | R1 | R₂ | R₃ |
|---|---|---|---|
| 23 | cyclopentyl | H₂N–CH₃ | –(CH₂)₄–N(piperazine)N–Et |
| 24 | cyclopentyl | 4-(Et₂N)-C₆H₄-CH₂-NH-CH₃ | –(CH₂)₄–N(piperazine)N–Et |
| 25 | cyclopentyl | 4-F-C₆H₄-CH₂-NH-CH₃ | –(CH₂)₄–N(piperazine)N–Et |
| 26 | cyclopentyl | 4-(H₃CO)-C₆H₄-CH₂-NH-CH₃ | –(CH₂)₄–N(piperazine)N–Et |
| 27 | cyclopentyl | 4-(Me₂N-CH₂)-C₆H₄-C(O)-NH-CH₃ | –(CH₂)₄–N(piperazine)N–Et |
| 29 | cyclopentyl | H₂N–CH₃ | –(CH₂)₄–N(pyrrolidine) |
| 30 | cyclopentyl | 4-(H₃CO)-C₆H₄-CH₂-NH-CH₃ | –(CH₂)₄–N(pyrrolidine) |
| 31 | cyclopentyl | 4-(Me₂N-CH₂)-C₆H₄-C(O)-NH-CH₃ | –(CH₂)₄–N(pyrrolidine) |
| 32 | cyclopentyl | 4-F-C₆H₄-CH₂-NH-CH₃ | –(CH₂)₄–N(pyrrolidine) |
| 33 | Et | H₂N–CH₃ | –(CH₂)₄–N(pyrrolidine) |

TABLE 1-continued

Compound with general formula (I) composition of the Invention

| Comp | R1 | R₂ | R₃ |
|---|---|---|---|
| 34 | Et | 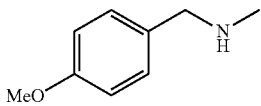 | 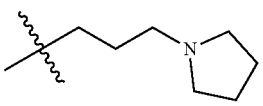 |
| 35 | Et | 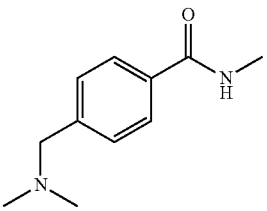 | 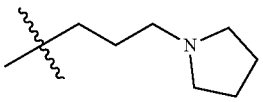 [SMILES: *CCCN1CCCC1] |
| 36 | Et | 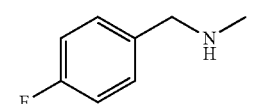 | 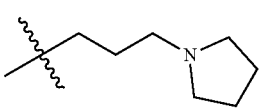 [SMILES: *CCCN1CCCC1] |
| 37 | 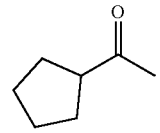 | H₂N— |  |
| 38 | 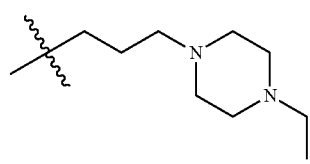 [SMILES: *CCCN1CCN(CC)CC1] | 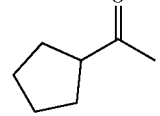 | 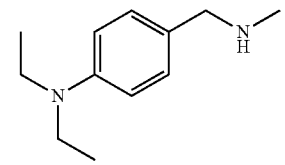 |
| 39 | 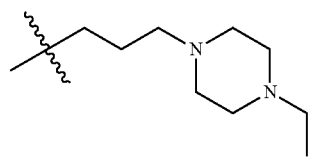 | 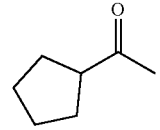 | 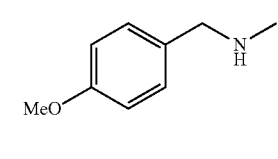 |
| 40 | 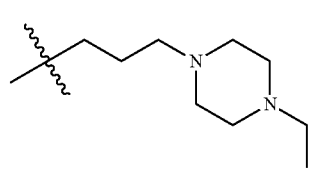 | 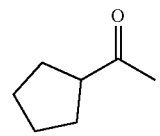 | 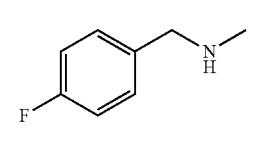 |

Experimental Procedure for Screening Toll-Like Receptor 9 Antagonistic Activity

A medium throughput biological assay based on toll-like receptor 9 activation has been designed in primary human immune cells to screen the synthesized small molecules with general formula (I) for toll-like receptor 9 (TLR9) antagonism. Among the immune cell subsets circulating in the peripheral blood, two cell subsets plasmacytoid dendritic cells (PDCs) and B lymphocytes has significant expression of TLR9. Plasmacytoid dendritic cells are capable of producing type I interferons (e.g. IFN-alpha) in response to TLR9 ligands. Type A and type B unmethylated cytosine-guanine rich DNA oligonucleotides (CpG oligonucleotides) are the bonafide ligands for TLR9.

Example 10

The assay is based on the principle that establishes production of IFN-alpha from human PBMC in response to type A CpG oligonucleotides (CpGA) almost exclusively results from TLR9 triggering on the PDCs (data not shown). In the screening assay we isolated PBMCs from venous blood collected from healthy donors using density gradient centrifugation. PBMCs were cultured the at 2-3*10^5 cells/ 200 ul/well in a 96 well plate. TLR9 agonist CpGA was added at 1 uM in presence of escalating doses of the synthesized small molecules (0 uM, 0.1 uM, 1 uM, 5 uM, 10 uM and 20 uM). The supernatants was collected after overnight culture from the culture wells and looked for IFN-alpha using enzyme linked immunosorbent assay (ELISA). In this screening assay, molecules having TLR9 antagonistic activity inhibited IFN-alpha production. The compounds used for the assay and the results were depicted in FIG. 1. For the biological validation of TLR9 antagonism the bona fide TLR9 agonist CpG oligonucleotides were used. As no standard marked small molecule antagonist for TLR9 exists, we did not use any standard compound.

Example 11

Experimental Procedure for TLR9 Reporter Assay

HEK-Blue-hTLR9 Secreted Alkaline Phosphatase (SEAP) reporter assay was used to screen compounds with general formula (I) for TLR9 antagonism. Reporter HEK cell lines expressing human TLR9 along with a NF-κB promoter driven secreted embryonic alkaline phosphatase (SEAP) reporter gene were used. A 96 well plate in complete DMEM medium supplemented with 100 µg/ml Normocin was used for overnight incubation of 70,000 cells/well at 37° C. and 5% $CO_2$. TLR9 agonist CpGB (ODN2006) was added after incubation to the wells at a concentration of 1 µM in presence of escalating doses of compounds with general formula (I) and subsequently incubated for 24 hours at 37° C. and 5% $CO_2$. Supernatants were collected and 20l of supernatant was added to wells containing 200 µl of Quanti-Blue detection media and further incubated for 2 hours. The OD values were taken at 620 nm in a spectrophotometer. TLR9 antagonistic activity was calculated based on inhibition of TLR9-mediated NF-kB activation in a dose-dependent manner (FIG. 2). The compounds used for the assay and the results were depicted in FIG. 2. For the biological validation of TLR9 antagonism the bona fide TLR9 agonist CpG oligonucleotides were used. As no standard marketed small molecule antagonist for TLR9 exists, we did not use any standard compound. For specificity the negative control was TLR7-expressing HEK293 reporter cells which were compared to the reporter activity of TLR9-expressing HEK293 reporter cells.

Example 12

Experimental Procedure for TLR9 Antagonism in Primary Human pDC.

A medium throughput biological assay was designed based on toll-like receptor 9 activation in plasmacytoid dendritic cells (pDC) isolated from PBMCs of healthy donors to screen compounds with general formula (I). pDCs were isolated from PBMCs by magnetic immune selection using anti-BDCA4 microbeads. The isolated pDCs were then cultured at 3*10^4 cells/100 µl/well in a 96 well plate. TLR9 agonist CpGA was added at 500 nM in presence of escalating doses of the compounds with general formula (I). Supernatants were collected after overnight culture from the culture wells and looked for IFN-alpha using enzyme linked immunosorbent assay (ELISA). TLR9 antagonistic activity was calculated based on inhibition of IFN-alpha production in this screening assay. The compounds used for the assay and the results were depicted in FIG. 3. For the biological validation of TLR9 antagonism the bona fide TLR9 agonist CpG oligonucleotides were used. As no standard marked small molecule antagonist for TLR9 exists, we did not use any standard compound.

Example 13

Experimental Procedure for Screening for Cytotoxicity of the Identified TLR9 Antagonists MTT assay is a widely used method for screening drugs and testing their cytotoxicity. MTT assay is a colorimetric assay for assessing cell viability. Under defined conditions, NAD(P)H-dependent cellular oxidoreductase enzymes may reflect the number of viable cells present. In viable cells with active metabolism, oxidoreductase enzymes are capable of reducing the tetrazolium dye MTT 3-(4, 5dimethylthiazol-2-yl)-2, 5-diphenyltetrazolium bromide to its insoluble purple colour formazan product with an absorbance maximum near 570 nm. Colour formation serves as a useful and convenient marker of only the viable cells since when cells die; they lose the ability to convert MTT into purple colour formazan. The exact cellular mechanism of MTT reduction into formazan is not well understood, but likely involves reaction with NADH or similar reducing molecules that transfer electrons to MTT (FIG. 4). HepG2 (a hepatic epithelial cell line) and SW480 (an intestinal mucosal epithelial cell line) cells were used to check cytotoxicity of the compounds with general formula (I). HepG2 and SW480 were cultured in DMEM Complete media in 96 well plates at density of 30,000 cells per well, making a final volume of 100 µl/well. Different concentrations (0.1, 0.5, 1, 10, 20 and 100 µM) of compounds with general formula (I) was added and subsequently incubated for 24 hours at 37° C. and 5% $CO_2$ in incubator. To each well 50 µl of MTT (5 mg/ml) was added and further incubated for 1 to 4 hours at 37° C. Thereafter, 100l of DMSO was added to each well with proper mixing to ensure complete solubilisation of formazan crystals. The absorbance was measured at 570 nm using an ELISA plate reader. TLR9 antagonists with general formula (I) did not showed any considerable cytotoxicity at concentrations below 100 µM on this assay (FIG. 4). The compounds used for the assay and the results were depicted in FIG. 4.

TABLE 2

Depicts $IC_{50}$ values of the compounds with general formula (I) composition of the Invention.

| Compound Number | $IC_{50}$ (µM) |
|---|---|
| 4 | 0.188 |
| 5 | 0.203 |
| 6 | 0.470 |
| 7 | 0.438 |
| 8 | 0.140 |
| 9 | 1.834 |
| 10 | 0.339 |
| 12 | 0.378 |
| 15 | 0.470 |
| 23 | 0.279 |
| 24 | 0.145 |
| 25 | 0.254 |
| 26 | 0.120 |
| 27 | 0.056 |
| 29 | 0.122 |
| 30 | 0.241 |
| 31 | 0.005 |
| 32 | 0.100 |
| 34 | 0.080 |
| 38 | 8.798 |

Advantages of the Invention

The synthesized new compounds with general formula (I) of the present invention have several advantages.
1. The compounds with general formula (I) can effect immune stimulation via TLR9 antagonism.
2. The compounds with general formula (I) are capable of inhibiting immune stimulation mediated through TLR9.
3. The compounds with general formula (I) can be evaluated by medium throughput biological assays involving human peripheral blood mononuclear cells, isolated human primary pDCs and reporter assay using transfected TLR9 cells. The assay system was standardized and the results from all three assay systems can be correlated.
4. The compounds with general formula (I) can be used in a number of clinical contexts for treating conditions involving unwanted immune activity in response to a suitable TLR ligand or TLR signalling agonist where inhibition of TLR9 mediated signalling is important.

We claim:

1. A compound of Formula 1 or pharmaceutically acceptable salts thereof,

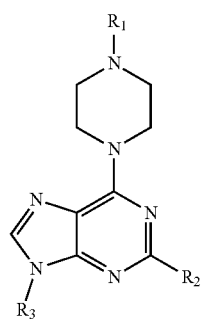

Formula (I)

wherein
R₁ is independently chosen from:

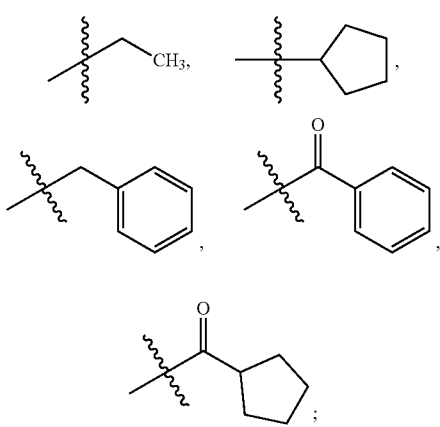

wherein
R₂ is independently chosen from:

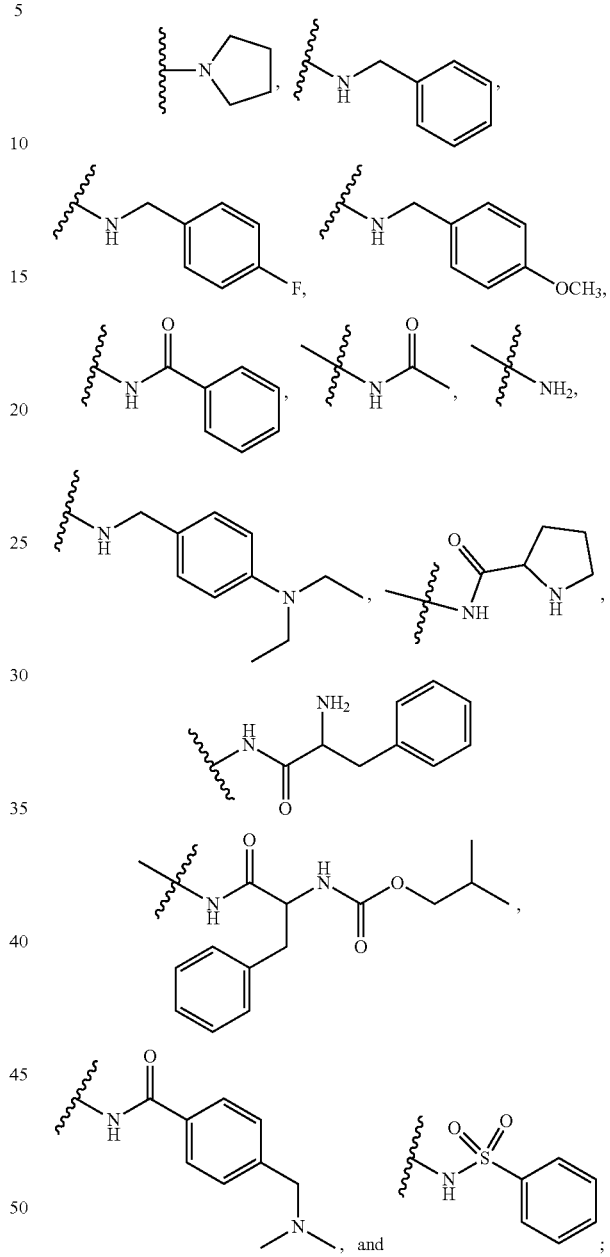

wherein
R₃ is independently chosen from:

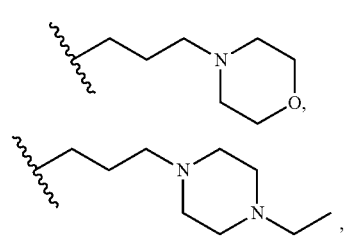

-continued

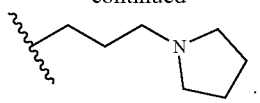

2. The compound of Formula 1 as claimed in claim 1, wherein the compound is selected from the group consisting of:
  6-(4-ethylpiperazin-1-yl)-9-(3-(4-ethylpiperazin-1-yl) propyl)-9H-purin-2-amine (compound 4);
  6-(4-ethylpiperazin-1-yl)-9-(3-(4-ethylpiperazin-1-yl) propyl)-N-(4-methoxybenzyl)-9H-purin-2-amine (compound 5);
  6-(4-ethylpiperazin-1-yl)-9-(3-(4-ethylpiperazin-1-yl) propyl)-N-(4-fluorobenzyl)-9H-purin-2-amine (compound 6);
  N-(4-(diethylamino)benzyl)-6-(4-ethylpiperazin-1-yl)-9-(3-(4-ethylpiperazin-1-yl)propyl)-9H-purin-2-amine (compound 7);
  N-benzyl-6-(4-ethylpiperazin-1-yl)-9-(3-(4-ethylpiperazin-1-yl)propyl)-9H-purin-2-amine (compound 8);
  6-(4-ethylpiperazin-1-yl)-9(3-(4-ethylpiperazin-1-yl)propyl-2-(pyrrolidin-1-yl)-9H-purine (compound 9);
  N-(6-(4-ethylpiperazin-1-yl)-9-(3-(4-ethylpiperazin-1-yl) propyl)-9H-purin-2-yl)benzamide (compound 10);
  N-(6-(4-ethylpiperazin-1-yl)-9-(3-(4-ethylpiperazin-1-yl) propyl)-9H-purin-2-yl) pyrrolidine-2-carboxamide (compound 12);
  N-(6-(4-ethylpiperazin-1-yl)-9-(3-(4-ethylpiperazin-1-yl) propyl)-9H-purin-2-yl) benzenesulfonamide (compound 13);
  N-(6-(4-ethylpiperazin-1-yl)-9-(3-(4-ethylpiperazin-1-yl) propyl)-9H-purin-2-yl)acetamide (compound 14);
  Iso-butyl (1-(6-(4-ethylpiperazin-1-yl)-9-(3-(4-ethylpiperazin-1-yl)propyl)-9H-purin-2-yl)amino)-1-oxo-3-phenylpropan-2-yl)carbamate (compound 15);
  4-((dimethylamino)methyl)-N-(6-(4-ethylpiperazin-1-yl)-9-(3-(4-ethylpiperazin-1-yl)propyl)-9H-purin-2-yl) benzamide (compound 16);
  (4-(2-amino-9-(3-(4-ethylpiperazin-1-yl)propyl)-9H-purin-6-yl)piperazin-1-yl)(phenyl)methanone (compound 18);
  4-(2-((4-(diethylamino)benzyl)amino-9-(3-(4-ethylpiperazin-1-yl)propyl)-9H-purine-6-yl)piperazin-1-yl)(phenyl)methanone (compound 19);
  (4-(9-(3-(4-ethylpiperazin-1-yl)propyl)-2-(pyrrolidin-1-yl)-9H-purin-6-yl)piperazin-1-yl)(phenyl)methanone (compound 20);
  (4-(9-(3-(4-ethylpiperazin-1-yl)propyl)-2-((4-methoxybenzyl)amino)-9H-purin-6-yl)piperazin-1-yl)(phenyl) methanone (compound 21);
  (4-(9-(3-(4-ethylpiperazin-1-yl)propyl)-2-((4-fluorobenzyl)amino)-9H-purin-6-yl)piperazin-1-yl)(phenyl) methanone (compound 22);
  6-(4-cyclopentylpiperazin-1-yl)-9-(3-(4-ethylpiperazin-1-yl)propyl)-9H-purin-2-amine (compound 23);
  6-(4-cyclopentylpiperazin-1-yl)-N-(4-diethylamino)benzyl)-9-(3-(4-ethylpiperazine-1-yl)propyl)-9H-purine-2-amine (compound 24);
  6-(4-cyclopentylpiperazin-1-yl)-9-(3-(4-ethylpiperazin-1-yl)propyl)-N-(4-fluorobenzyl)-9H-purin-2-amine (compound 25);
  6-(4-cyclopentylpiperazin-1-yl)-9-(3-(4-ethylpiperazin-1-yl)propyl)-N-(4-methoxybenzyl)-9H-purin-2-amine (compound 26);
  N-(6-(4-cyclopentylpiperazin-1-yl)-9-(3-(4-ethylpiperazin-1-yl)propyl)-9H-purin-2-yl)-4-((dimethylamino) methyl)benzamide (compound 27);
  6-(4-cyclopentylpiperazin-1-yl)-9-(3-(pyrrolidin-1-yl) propyl)-9H-purin-2-amine (compound 29);
  6-(4-cyclopentylpiperazin-1-yl)-N-(4-methoxybenzyl)-9-(3-(pyrrolidin-1-yl)propyl)-9H-purin-2-amine (compound 30);
  N-(6-(4-cyclopentylpiperazin-1-yl)-9-(3-(pyrrolidin-1-yl) propyl)-9H-purin-2-yl)-4-((dimethylamino)methyl) benzamide (compound 31);
  6-(4-cyclopentylpiperazin-1-yl)-N-(4-fluorobenzyl)-9-(3-(pyrrolidin-1-yl)propyl)-9H-purin-2-amine (compound 32);
  6-(4-ethylpiperazin-1-yl)-9-(3-(pyrrolidin-1-yl)propyl)-9H-purin-2-amine (compound 33);
  6-(4-ethylpiperazin-1-yl)-N-(4-methoxybenzyl)-9-(3-(pyrrolidin-1-yl)propyl)-9H-purin-2-amine (compound 34);
  4-((dimethylamino)methyl)-N-(6-(4-ethylpiperazin-1-yl)-9-(3-(pyrrolidin-1-yl)propyl)-9H-purin-2-yl)benzamide (compound 35);
  6-(4-ethylpiperazin-1-yl)-N-(4-fluorobenzyl)-9-(3-(pyrrolidin-1-yl)propyl)-9H-purin-2-amine (compound 36);
  (4-(2-Amino-9-(3-(4-ethylpiperazin-1-yl)propyl)-9H-purin-6-yl)piperazin-1-yl)(cyclopentyl)methanone (compound 37);
  Cyclopentyl(4-(2-(4-(diethylamino)benzylamino)-9-(3-(4-ethylpiperazin-1-yl)propyl)-9H-purin-6-yl)piperazin-1-yl)methanone (compound 38);
  Cyclopentyl(4-(9-(3-(4-ethylpiperazin-1-yl)propyl)-2-(4-methoxybenzylamino)-9H-purin-6-yl)piperazin-1-yl) methanone (compound 39); and
  Cyclopentyl(4-(9-(3-(4-ethylpiperazin-1-yl)propyl)-2-((4-fluorobenzyl)amino)-9H-purin-6-yl)piperazin-1-yl)methanone (compound 40).

3. A method of treating an auto-immune disease associated with TLR9 activation in a subject in need thereof, the method comprising providing an effective amount of the compound of claim 1 to the subject.

4. A method of inhibiting TLR9-mediated immune-stimulatory signaling, the method comprising contacting a cell expressing TLR9 with an effective amount of the compound of claim 1.

5. A process for preparation of the compound of Formula 1 of claim 1, the method comprising:
  (i) reacting 6-chloro-9H-purin-2-amine, (compound 1), with ethyl piperazine or 1-(3-chloropropyl)-4-ethylpiperazine in presence of a base in a solvent at reflux temperature for a period ranging between 3 to 4 hrs to obtain 6-(4-ethylpiperazine-1-yl)-9H-purin-2-amine (compound 2) or 6-chloro-9-(3-(4-ethylpiperazin-1-yl) propyl)-9H-purin-2-amine (compound 17);
  (ii) reacting compound 2 with 1-bromo-3-chloro propane in presence of a base in DMSO, DMF at room temperature for a period ranging between 10 to 12 hrs to obtain 9-(3-chloropropyl)-6-(4-ethylpiperazine-1-yl)-9H-purin-2-amine (compound 3);
  (iii) reacting compound 3 with ethyl piperazine or pyrrolidine in presence of a base DIPEA or Et$_3$N in a solvent to obtain 6-(4-ethylpiperazin-1-yl)-9-(3-(4-ethylpiperazin-1-yl)propyl)-9H-purin-2-amine (compound 4) or 6-(4-ethylpiperazin-1-yl)-9-(3-(pyrrolidin-1-yl)propyl)-9H-purin-2-amine (compound 33) respectively;
  (iv) reacting compound 4 as obtained in (iii) with a compound selected from the group consisting of aromatic aldehyde, acid, acid chloride, and dibromoalkane in presence of a base and a solvent at a temperature range between 25 to 110° C., for a period ranging between 3 to 24 hrs to obtain:

a. 6-(4-ethylpiperazin-1-yl)-9-(3-(4-ethylpiperazin-1-yl)propyl)-N-(4-methoxybenzyl)-9H-purin-2-amine (compound 5);
b. 6-(4-ethylpiperazin-1-yl)-9-(3-(4-ethylpiperazin-1-yl)propyl)-N-(4-fluorobenzyl)-9H-purin-2-amine (compound 6);
c. N-(4-(diethylamino)benzyl)-6-(4-ethylpiperazin-1-yl)-9-(3-(4-ethylpiperazin-1-yl)propyl)-9H-purin-2-amine (compound 7);
d. N-benzyl-6-(4-ethylpiperazin-1-yl)-9-(3-(4-ethylpiperazin-1-yl)propyl)-9H-purin-2-amine (compound 8);
e. 6-(4-ethylpiperazin-1-yl)-9(3-(4-ethylpiperazin-1-yl)propyl-2-(pyrrolidin-1-yl)-9H-purine (compound 9);
f. N-(6-(4-ethylpiperazin-1-yl)-9-(3-(4-ethylpiperazin-1-yl)propyl)-9H-purin-2-yl)benzamide (compound 10);
g. tert-butyl 2-((6-(4-ethylpiperazin-1-yl)-9-(3-(4-ethylpiperazin-1-yl)propyl)-9H-purin-2-yl)carbamoyl)pyrrolidine-1-carboxylate (compound 11),
h. N-(6-(4-ethylpiperazin-1-yl)-9-(3-(4-ethylpiperazin-1-yl)propyl)-9H-purin-2-yl)pyrrolidine-2-carboxamide (compound 12);
i. N-(6-(4-ethylpiperazin-1-yl)-9-(3-(4-ethylpiperazin-1-yl)propyl)-9H-purin-2-yl)benzenesulfonamide (compound 13);
j. N-(6-(4-ethylpiperazin-1-yl)-9-(3-(4-ethylpiperazin-1-yl)propyl)-9H-purin-2-yl)acetamide (compound 14);
k. Iso-butyl (1-(6-(4-ethylpiperazin-1-yl)-9-(3-(4-ethylpiperazin-1-yl)propyl)-9H-purin-2-yl)amino)-1-oxo-3-phenylpropan-2-yl)carbamate (compound 15); or
l. 4-((dimethylamino)methyl)-N-(6-(4-ethylpiperazin-1-yl)-9-(3-(4-ethylpiperazin-1-yl)propyl)-9H-purin-2-yl)benzamide (compound 16);

(v) reacting compound 1 or compound 17 with a compound phenyl (piperazine-1-yl)methanone, 1-cyclopentylpiperazine, or cyclopentyl(piperazin-1-yl)methanone in presence of a base selected from $Cs_2CO_3$ or $K_2CO_3$ in a solvent selected from THF, dioxane, or $CH_3CN$ at a temperature ranging between 80 to 100° C. to obtain:

a. (4-(2-amino-9-(3-(4-ethylpiperazin-1-yl)propyl)-9H-purin-6-yl)piperazin-1-yl)(phenyl)methanone (compound 18);
b. 6-(4-cyclopentylpiperazin-1-yl)-9-(3-(4-ethylpiperazin-1-yl)propyl)-9H-purin-2-amine (compound 23);
c. 6-(4-cyclopentylpiperazin-1-yl)-9H-purin-2-amine (compound 28); or
d. (4-(2-Amino-9-(3-(4-ethylpiperazin-1-yl)propyl)-9H-purin-6-yl)piperazin-1-yl)(cyclopentyl)methanone (compound 37);

(vi) reacting compound 18 or compound 23 with a compound selected from the group consisting of aldehyde, acid and dibromo alkane in a solvent and in the presence of a base at a temperature ranging between 80 to 110° C. for a period ranging between 12 to 24 hrs to obtain:

a. 4-(2-((4-(diethylamino)benzyl)amino-9-(3-(4-ethylpiperazin-1-yl)propyl)-9H-purine-6-yl)piperazin-1-yl)(phenyl)methanone (compound 19);
b. (4-(9-(3-(4-ethylpiperazin-1-yl)propyl)-2-(pyrrolidin-1-yl)-9H-purin-6-yl)piperazin-1-yl)(phenyl)methanone (compound 20);
c. (4-(9-(3-(4-ethylpiperazin-1-yl)propyl)-2-((4-methoxybenzyl)amino)-9H-purin-6-yl)piperazin-1-yl)(phenyl)methanone (compound 21);
d. (4-(9-(3-(4-ethylpiperazin-1-yl)propyl)-2-((4-fluorobenzyl)amino)-9H-purin-6-yl)piperazin-1-yl)(phenyl)methanone (compound 22);
e. 6-(4-cyclopentylpiperazin-1-yl)-N-(4-diethylamino)benzyl)-9-(3-(4-ethylpiperazine-1-yl)propyl)-9H-purine-2-amine (compound 24);
f. 6-(4-cyclopentylpiperazin-1-yl)-9-(3-(4-ethylpiperazin-1-yl)propyl)-N-(4-fluorobenzyl)-9H-purin-2-amine (compound 25);
g. 6-(4-cyclopentylpiperazin-1-yl)-9-(3-(4-ethylpiperazin-1-yl)propyl)-N-(4-methoxybenzyl)-9H-purin-2-amine (compound 26); or
h. N-(6-(4-cyclopentylpiperazin-1-yl)-9-(3-(4-ethylpiperazin-1-yl)propyl)-9H-purin-2-yl)-4-((dimethylamino)methyl)benzamide (compound 27);

(vii) reacting compound 28 with 1-(3-chloropropyl)pyrrolidine to give 6-(4-cyclopentylpiperazin-1-yl)-9-(3-(pyrrolidin-1-yl)propyl)-9H-purin-2-amine (compound 29), and (viii) reacting compound 29, compound 33 or compound 37 with a compound of aldehyde or an acid in presence of a solvent and a base, at a temperature ranging between 25 to 100° C., for a period ranging between 3 hr to 24 hr to obtain:

a. 6-(4-cyclopentylpiperazin-1-yl)-N-(4-methoxybenzyl)-9-(3-(pyrrolidin-1-yl)propyl)-9H-purin-2-amine(compound 30);
b. N-(6-(4-cyclopentylpiperazin-1-yl)-9-(3-(pyrrolidin-1-yl)propyl)-9H-purin-2-yl)-4-((dimethylamino)methyl)benzamide (compound 31);
c. 6-(4-cyclopentylpiperazin-1-yl)-N-(4-fluorobenzyl)-9-(3-(pyrrolidin-1-yl)propyl)-9H-purin-2-amine (compound 32);
d. 6-(4-ethylpiperazin-1-yl)-N-(4-methoxybenzyl)-9-(3-(pyrrolidin-1-yl)propyl)-9H-purin-2-amine (compound 34);
e. 4-((dimethylamino)methyl)-N-(6-(4-ethylpiperazin-1-yl)-9-(3-(pyrrolidin-1-yl)propyl)-9H-purin-2-yl)benzamide (compound 35);
f. 6-(4-ethylpiperazin-1-yl)-N-(4-fluorobenzyl)-9-(3-(pyrrolidin-1-yl)propyl)-9H-purin-2-amine (compound 36);
g. Cyclopentyl(4-(2-(4-(diethylamino)benzylamino)-9-(3-(4-ethylpiperazin-1-yl)propyl)-9H-purin-6-yl)piperazin-1-yl)methanone (compound 38);
h. Cyclopentyl(4-(2-(4-(diethylamino)benzylamino)-9-(3-(4-ethylpiperazin-1-yl)propyl)-9H-purin-6-yl)piperazin-1-yl)methanone (compound 39); or
i. Cyclopentyl(4-(9-(3-(4-ethylpiperazin-1-yl)propyl)-2-((4-fluorobenzyl)amino)-9H-purin-6-yl)piperazin-1-yl)methanone (compound 40).

6. The process as claimed in claim 5, wherein the base of (i) and (ii) is selected from the group consisting of $Cs_2CO_3$ and $K_2CO_3$.

7. The process as claimed in claim 5, wherein the solvent of (i) is selected from the group consisting of acetonitrile, THF, dioxane, and DMF.

8. The process as claimed in claim 5, wherein the solvent of (iii) is selected from the group consisting of toluene and DCM.

9. The process as claimed in claim 5, wherein the aromatic aldehyde, acid, acid chloride, and dibromo alkane of (iv) are selected from the group consisting of benzaldehyde, p-anisaldehyde, 4-fluorobenzaldehyde, 4-diethylamino benzaldehyde, benzoyl chloride, 1-(Tert-butoxycarbonyl) pyrrolidine-2-carboxylic acid, benzenesulphonyl chloride, acetyl chloride, 2-(Isobutoxycarbonyl)amino)-3-phenyl propionic acid dibromopropane, 4-[(Dimethylamino)methyl] benzaldehyde, 1, 4-dibromobutane, and 4-[(Dimethylamino) methyl]benzoic acid.

10. The process as claimed in claim 5, wherein the base of (iv), (vi) and (viii) are selected from the group consisting of pyridine, sodium hydride, sodium triacetoxy borohydride, sodium cyanoborohydride, and sodium borohydride.

11. The process as claimed in claim 5, wherein the solvent of (iv), (vi) and (viii) is selected from the group consisting of toluene, dichloromethane, THF, and DMF.

12. A pharmaceutical composition comprising an effective amount of the compounds of Formula 1 as claimed in claim 1 or pharmaceutically acceptable salts thereof, individually or in combination, optionally along with one or more pharmaceutically acceptable additives, carriers or diluents.

13. The process as claimed in claim 5, wherein the aldehyde of step (vi) and (viii) is selected from the group consisting of benzaldehyde, p-anisaldehyde, 4-fluorobenzaldehyde and 4-diethylamino benzaldehyde; and the acid of step (vi) and (viii) is selected from the group consisting of 1-(Tert-butoxycarbonyl)pyrrolidine-2-carboxylic acid, 2-(Isobutoxycarbonyl)amino)-3-phenyl propionic acid, and 4-[(Dimethylamino) methyl]benzoic acid.

14. The process as claimed in claim 5, wherein the dibromo alkane of step (vi) is selected from the group consisting of dibromopropane and 1, 4-dibromobutane.

* * * * *